(12) United States Patent
Ramaswamy et al.

(10) Patent No.: US 11,376,347 B1
(45) Date of Patent: Jul. 5, 2022

(54) MATERIALS AND METHODS FOR ACCELERATING CARDIOVASCULAR TISSUE REGENERATION

(71) Applicants: Sharan D. Ramaswamy, Miami, FL (US); Brittany Gonzalez, Miami, FL (US); Ariadna Herrera, Miami, FL (US); Alexander Williams, Miami, FL (US)

(72) Inventors: Sharan D. Ramaswamy, Miami, FL (US); Brittany Gonzalez, Miami, FL (US); Ariadna Herrera, Miami, FL (US); Alexander Williams, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/353,006

(22) Filed: Jun. 21, 2021

(51) Int. Cl.
| | |
|---|---|
| *A61L 27/36* | (2006.01) |
| *A61L 27/26* | (2006.01) |
| *A61L 27/24* | (2006.01) |
| *A61L 27/22* | (2006.01) |
| *C12N 5/0775* | (2010.01) |

(52) U.S. Cl.
CPC ......... *A61L 27/3633* (2013.01); *A61L 27/227* (2013.01); *A61L 27/24* (2013.01); *A61L 27/26* (2013.01); *A61L 27/36* (2013.01); *A61L 27/3629* (2013.01); *A61L 27/3683* (2013.01); *C12N 5/0663* (2013.01); *A61L 2430/20* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 7,795,027 B2* | 9/2010 | Hiles | ................... | A61L 27/3629 435/395 |
| 2001/0051824 A1* | 12/2001 | Hopkins | ............. | A61L 27/3895 623/2.13 |
| 2002/0115208 A1* | 8/2002 | Mitchell | .............. | C12N 5/0068 435/325 |
| 2020/0121828 A1* | 4/2020 | Qin | ..................... | A61L 27/3691 |

OTHER PUBLICATIONS

Chang etal, PLOS ONe, 2016, 11(4), e0153412. (Year: 2016).*
Giselle C. Yeo., et al., "The elastin matrix in tissue engineering and regeneration." Current Opinion in Biomedical Engineering, 2018, 6:27-32.
Brittany A. Gonzalez, et al., "Physiologically Relevant Fluid-Induced Oscillatory Shear Stress Stimulation of Mesenchymal Stem Cells Enhances the Engineered Valve Matrix Phenotype." Frontiers in Cardiovascular Medicine, 2020, 7(69):1-14.
Sasmita Rath., et al., "Differentiation and Distribution of Marrow Stem Cells in Flex-Flow Environments Demonstrate Support of the Valvular Phenotype." PLoS one, 2015, 10(11):1-19.
Alexander Williams., et al., "A "sweet-spot" for fluid-induced oscillations in the conditioning of stem cell-based engineered heart valve tissues" Journal of Biomechanics, 2017, 65:40-48.
Brittany A. Gonzalez., et al., "Porcine Small Intestinal Submucosa Mitral Valve Material Responses Support Acute Somatic Growth." Tissue Engineering, 2020, 00(00):1-15.

* cited by examiner

*Primary Examiner* — Allison M Fox
(74) *Attorney, Agent, or Firm* — Saliwanchik, Lloyd & Eisenschenk

(57) ABSTRACT

Provided are elastin-rich bioscaffolds, enhanced via stem cell pre-seeding and flow-based mechanical conditioning followed by subsequent removal of stem cells. The bioscaffolds may accelerate cardiovascular tissue regeneration and can be used in the surgical repair/reconstruction in various cardiovascular and other surgical applications including heart valves, cardiovascular grafts, and patches. The provided acellular, elastin-rich bioscaffold will pose minimal immune risk and reduced FDA regulatory hurdles as a non-living biologic product.

16 Claims, 30 Drawing Sheets
(30 of 30 Drawing Sheet(s) Filed in Color)

MATERIALS AND METHODS FOR ACCELERATING CARDIOVASCULAR TISSUE REGENERATION

BACKGROUND

Critical valve diseases in the young have no viable treatment option owing to the absence of small sizing options and the inability of prosthetic valves to accommodate the growth of the child. Manually assembled replacement mitral valves made of porcine small intestinal submucosa (PSIS) bioscaffold material (Cormatrix Inc., Roswell, Ga.) have been implanted (e.g., into a juvenile baboon model) to assess potential to provide somatic growth. After 20-months post-implant PSIS valves have been found to function reasonably well in supporting growth of the animal, but in some cases failed owing to hostile immune responses due to remnants of porcine cellular debris still residing on the bioscaffold and an insufficient rate of host tissue remodeling to enable de novo valve tissue formation.

BRIEF SUMMARY

Congenital heart problems affect 8 out of 1000 live births in the United States, making them one of the most common types of birth abnormalities (www.aha.org). Due to the unavailability of small prosthetic valves and a lack of artificial valves that adapt to somatic growth, clinical solutions for congenital heart problems are limited. Tissue engineered heart valves are of interest as an approach for replacing defective heart valves as they allow self-repair and growth. Porcine small intestinal submucosa (PSIS) can be used as a viable bioscaffold in an animal model. Explants of a PSIS mitral valve have displayed a chronic immune response, hypothesized to be due to remaining porcine cells (see, e.g., Gonzalez et. al., Porcine small intestinal submucosa mitral valve material responses support acute somatic growth, Tissue Engineering Part A. doi: 10.1089/ten.tea.2019.0220, 2020, which is hereby incorporated by reference herein in its entirety.).

Embodiments of the subject invention provide advantageous decellularization techniques for removing porcine cells while maintaining the integrity of the extracellular matrix (ECM), thus providing an acellular scaffold (e.g., a PSIS scaffold) that has a structurally intact ECM. Advantageously, the scaffold can be used for implantation little or no corresponding immune response, thereby facilitating proper de novo valvular tissue formation via chemotaxis.

In an embodiment, an enriched decellularized bioscaffold implant for implantation in a patient can comprise: a decellularized tissue matrix; and an ECM component generated by stem cells. The decellularized tissue matrix can be synthetic, xenogeneic, or allogeneic to the patient, and the stem cells can be allogeneic, autologous, or syngeneic to the patient. The enhanced ECM component can be elastin, collagen, glycosaminoglycans, or a combination thereof. The decellularized tissue matrix can be, for example, PSIS. The decellularized tissue matrix can have a cylindrical shape comprising a radial direction and a circumferential direction, and can have a measurable average maximum tensile stress in the circumferential direction, which is at least 80% of a measurable average maximum tensile stress of the decellularized tissue matrix in the radial direction. A group of the enriched decellularized bioscaffold implants can have an average percentage elastin not less than an average percentage elastin of a control group of (similar) enriched but non-decellularized bioscaffold implants. The group of enriched decellularized bioscaffold implants can have an average percentage collagen not less than an average percentage collagen of the control group.

In another embodiment, a method of fabricating an enriched decellularized bioscaffold implant for implantation in a patient can comprise: providing a tissue matrix; exposing the tissue matrix to stem cells in a bioreactor under conditions sufficient to generate an enhanced ECM component in the tissue matrix; and decellularizing the tissue matrix to remove the stem cells while maintaining the enhanced ECM component in the tissue matrix. The conditions sufficient to generate an enhanced ECM component in the tissue matrix can comprise mechanical stimulation at a targeted fluid-induced oscillatory shear stress range having an oscillatory shear index (OSI) in a range of from 0.18 to 0.23 (e.g., from 0.19 to 0.21). The tissue matrix can be xenogeneic to the patient, and/or the stem cells can be allogeneic to the patient. The tissue matrix can comprise, for example, PSIS. The enhanced ECM component can comprise elastin, collagen, or glycosaminoglycans.

In another embodiment, an enriched decellularized bioscaffold implant for implantation in a patient can comprise: a decellularized tissue matrix; and an ECM component generated by stem cells; the enhanced ECM component comprising elastin and collagen; the patient being a human patient; the stem cells being allogeneic to the patient; the decellularized tissue matrix being PSIS; the decellularized tissue matrix having a cylindrical shape comprising a radial direction and a circumferential direction; and the decellularized tissue matrix having a measurable average maximum tensile stress in the circumferential direction, which is at least 80% of a measurable average maximum tensile stress of the decellularized tissue matrix in the radial direction. The decellularized bioscaffold implant can have a percentage elastin after decellularization not less than its percentage elastin before decellularization; the decellularized bioscaffold implant can have a percentage collagen after decellularization not less than its percentage collagen before decellularization; and/or the decellularized bioscaffold implant can have a cell count after decellularization at least 50% less than its cell count after generation of the elastin and collagen but before decellularization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a tissue sample at 20× magnification before decellularization and FIG. 1B shows a tissue sample at 20× magnification after decellularization.

DETAILED DESCRIPTION

Figure 1A:
FIGS. 1A-1B show the careful removal of stem cells (decellularization) while leaving the engineered tissues or engineered extracellular matrix intact.

Embodiments of the subject invention combine recent advances including tubular bioscaffold valve construction (Cormatrix, Roswell, Ga.), Flow-Stretch-Flex bioreactors, and oscillatory flow mechanobiology with a novel careful decellularization procedure applied to novel engineered tissues with elastin production via stem cells with flow-based conditioning to provide uniquely advantageous surgical implants. Certain aspects of embodiments of the subject invention are related to U.S. provisional application Ser. No. 62/947,379, filed Dec. 12, 2019, and U.S. patent application Ser. No. 17/119,170, filed Dec. 11, 2020, each of which is hereby incorporated by reference herein in its entirety.

Embodiments may produce elastin-rich tissues, advantageously of the same species as the host in which it will be implanted, for cardiovascular repair or regenerative applications, using stem cells and safely removing the stem cells from the engineered tissue matrix prior to implantation.

In certain embodiments, methods can facilitate the removal of the stem cells (e.g., decellularization) while leaving the engineered tissues or engineered extracellular matrix (ECM) intact, relatively more intact, less damaged, or in a desirable condition as compared to existing methods. A major ECM component found to have increased production within the tissue engineered construct is elastin, which has been shown to help accelerate the regeneration of cardiovascular tissues after the construct is implanted for repair or regeneration purposes.

Embodiments provide a decellularization process that retains the integrity of fibers in an tissue engineered construct and may re-align fibers from the radial to circumferential direction resulting in a more isotropic material in terms of its maximum strength. Without being bound by theory, the radial fibers may not be lost, but rather they are re-distributed.

Embodiments can safely remove stem cells while retaining the critical increased engineered elastin content that the cells had produced via the bioreactor dynamic tissue culture conditions, which can potentially accelerate the regeneration of cardiovascular tissues.

Thus, in preferred embodiments, methods can provide elastin-rich tissues of the same species as the host in which it will be implanted for cardiovascular repair/regenerative applications, using stem cells and removing the stem cells from the engineered tissue matrix, prior to implantation. The careful removal of the stem cells may refer to decellularization. Careful in this context means that cells are removed but the tissue structure (e.g., collagen and elastin) remains intact. Elastin is a major ECM component that may be increased within a tissue engineered construct in accordance with the subject invention. Elastin can help accelerate the regeneration of cardiovascular tissues after the construct is implanted for repair/regeneration purposes.

In certain embodiments a flex-flow-stretch bioreactor may induce oscillatory flow shear stresses on porcine small intestinal submucosa (PSIS) tubular valves pre-seeded with allogeneic bone marrow-derived stem cells (e.g., allogeneic to the intended recipient, or derived from the same species in which the valve will be eventually implanted). Embodiments have demonstrated that the PSIS bioscaffold was covered in engineered ECM material, which was composed of several biomolecules, particularly collagen and elastin proteins. In vitro elastin production is not easily feasible but has been demonstrated in accordance with embodiments of the subject invention and may be key in accelerating valve regeneration rates after implantation, since elastin is a known driver of chemotaxis and beneficial tissue remodeling.

Embodiments may provide engineered ECM material containing rich elastin components derived from allogeneic stem cells, (e.g., cells that are of the same species as the intended recipient; e.g. human), thereby augmenting biocompatibility and reducing the risk of a hostile immune response.

In certain embodiments, because stem cell viability in cardiovascular structures may be low and the engineered ECM with elastin protein has been facilitated in vitro, the stem cells may be removed using a careful decellularization process that may retain some, most, or all of the stem cell-secreted ECM components while removing some, most, or all of the stem cells. Advantageously, the stem cell secreted ECM is retained, including components such as elastin, which are critical drivers in ensuring that chemotaxis occurs in vivo, to promote accelerated heart valve tissue regeneration. Decellularization of the stem cells may also serve to minimize uncertainties with immune responses and enable a repeatable and scalable technology, with a more favorable regulatory pathway.

Embodiments provide de novo elastin production and 'careful decellularization' which are applicable to cardiovascular applications beyond heart valves (e.g., applications where accelerated regeneration is essential both in children as well as in adults) and may also be applicable and advantageous outside cardiovascular applications. As described in Yeo, et al., (The elastin matrix in tissue engineering and regeneration, Current Opinion in Biomedical Engineering, Volume 6, 2018, Pages 27-32, ISSN 2468-4511, https://doi.org/10.1016/j.cobme.2018.02.007; which is hereby incorporated herein by reference in its entirety), the elastin matrix crucially confers mechanical strength, elasticity, organization and biological signaling to almost all connective tissues, which are matched to specific tissue biomechanical and functional requirements. However, elastin is often poorly restored during native tissue repair due to low elastin production and assembly by post-neonatal and mature cells. Consequently, interventional strategies towards tissue regeneration often incorporate exogenous elastin or promote the production of endogenous elastin, in order to mimic the composition, architecture, and function of native tissues. Current strategies include the use of decellularized elastin-containing tissue, synthetic tropoelastin or elastin-containing materials and approaches that stimulate de novo elastin deposition.

In certain embodiments, a bioscaffold can be provided that is elastin-rich, via stem cell pre-seeding and flow-based, mechanical conditioning and subsequent removal of stem cells, which may accelerate cardiovascular tissue regeneration, and can be used in the surgical repair/reconstruction in various cardiovascular applications (e.g.,. heart valves, cardiovascular grafts, patches, etc.). The acellular, elastin-rich bioscaffold poses minimal immune risk and reduced FDA regulatory hurdles as a non-living biologic product. This provides a potentially permanent approach to cardiovascular and other surgical applications where tissue regeneration is needed.

Embodiments allow for robust elastin production via mechanical stimulation at a targeted fluid-induced oscillatory shear stress range (e.g., quantified in an oscillatory shear index (OSI) of $0.18 \leq OSI \leq 0.23$), optionally at an OSI of 0.17, 0.19, 0.20, 0.21, 0.22, 0.24, including ranges, combinations, or permutations thereof. (See, e.g., Williams et al., A sweet-spot for fluid-induced oscillations in the conditioning of stem cell-based engineered heart valve tissues, J Biomech, 2017 Dec. 8; 65:40-48; which is hereby incorporated herein by reference in its entirety).

The bioscaffold may have cells removed (e.g., decellularized) after the stem cells have secreted the augmented ECM components. These species-derived ECM components contained within a non-living biologic product may provide bio-chemical signals to accelerate de novo cardiovascular or other tissue formation, which in turn promotes the surgical repair or reconstruction treatment.

Figure 13:
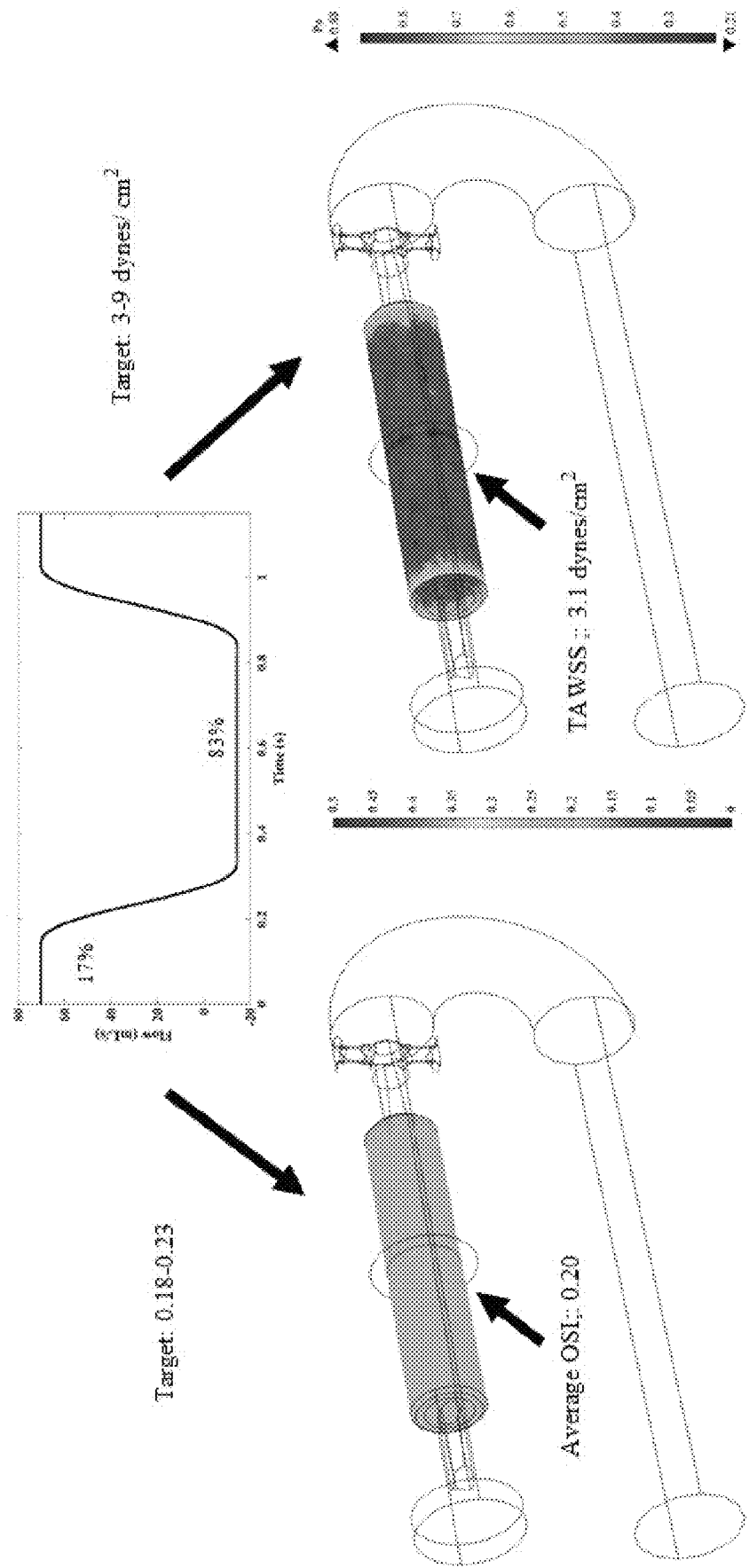
FIG. 13 shows the design and results of a computational fluid dynamics (CFD) analysis of an in-house bioreactor design

In one embodiment, stem cells can be collected and isolate (e.g., bone marrow aspirates can be collected, and stem cells isolated), e.g., via multiple centrifugation steps. Once isolated, the stem cells are cultured and grown to confluency. The stem cells are then seeded onto the scaffolds and placed onto a support structure. The stem cell-seeded scaffold constructs are subsequently inserted or immersed in conical tubes containing tissue culture media. Next, the conical tubes are placed in a rotisserie culture system for 8 days. After 8 days, the stem cell -seeded scaffolds are placed in a bioreactor system and exposed to an OSI of 0.20 and a time averaged wall shear stress (TAWSS) of 3.1 dynes/cm$^2$ for 14 days. Possible ranges for TAWSS are indicated in FIG. 13, where the target ranges between 3 to 9 dynes/cm$^2$, alternatively 2, 4, 5, 6, 7, 8, or 10 dynes/cm$^2$, including increments, combinations, and ranges of any of the foregoing (see, e.g., Williams et al., supra.).

Based on the results of experiments disclosed herein, in some embodiments, a meaningful bioreactor system exposure duration is 14 days, as comparable amounts (p>0.05) of elastin and collagen compared to native heart valve tissues have been shown with the tested embodiments. More reasonable exposure times may be applied for clinical and commercial use based on the application and the amount of elastin needed for the application. By way of non-limiting examples, exposure durations of less than 1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, including increments, combinations, and ranges of any of the foregoing, are contemplated within the scope of the subject invention. By way of further non-limiting examples, exposure durations of less than 1, 1, 2, 3, 4, 5, 6, 7, 8, 9, 10, 11, 12, 13, 14, 15, 16, 17, 18, 19, 20, 21, 22, 23, 24, or more hours, including increments, combinations, and ranges of any of the foregoing, are contemplated within the scope of the subject invention. By way of further non-limiting examples, exposure durations of less than 1, 1, 2, 3, 4, or more weeks, including increments, combinations, and ranges of any of the foregoing, are contemplated within the scope of embodiments of the subject invention.

Embodiments provide a single exposure period, alternatively, 2, 3, 4, or more exposure periods, including increments, combinations, and ranges of any of the foregoing, are contemplated within the scope of the subject invention.

This conditioning has been shown to lead to the deposition of de novo cardiovascular ECM components on the bioscaffold substrate, including the vital elastin protein (see, e.g., Gonzalez et. al., Physiologically-Relevant Fluid-Induced Oscillatory Shear Stress Stimulation of Mesenchymal Stem Cells Enhances the Engineered Valve Matrix Phenotype, Front. Cardiovasc. Med., doi: 10.3389/fcvm.2020.00069, 2020; which is hereby incorporated by reference herein in its entirety).

These bioscaffolds are then removed of the stem cells via a simple careful decellularization protocol as follows: place bioscaffold in 1% Triton-X 100 for 12 hours, while mixing, and rinse in PBS for 24 hours (change PBS at 12 hours) thereafter.

The range of surfactant concentration of Triton-X 100 must be considered carefully (e.g., in some embodiments, less than or equal to 1%) due to its toxicity, which can destroy the ECM. Since embodiments have demonstrated 1% as efficient in removing cellular components, while not removing a significant amount of ECM components in some embodiments a concentration of 1% Triton-X 100, alternatively 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0% or more Triton-X 100, including increments, combinations, and ranges of any of the foregoing, is provided.

In an embodiment, a surfactant contact time of 24 hrs is provided, since it demonstrated more cell removal than 12 hrs, while having the ECM remain intact. The range of surfactant contact time must be considered carefully (e.g., in some embodiments, less than or equal to 24 hrs) due to potential for toxicity, which can destroy the ECM. Since embodiments have demonstrated 24 hrs as efficient in removing cellular components, while not removing a significant amount of ECM components, in some embodiments a contact time of 24 hrs is provided. By way of non-limiting examples, surfactant contact times of less than 1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more hours, including increments, combinations, and ranges of any of the foregoing, are contemplated within the scope of the subject invention Exposing the surfactant to the bioscaffold for longer exposure times (e.g., greater than 24 hrs in some embodiments) must be considered carefully to manage potential toxicity. If a shorter time (e.g., less than 12 hrs in some embodiments) is chosen, then the risk of not being able to remove sufficient amounts of the cellular components, allowing for an immune response to occur once implanted, must be considered.

For rinsing agents, PBS is a good choice as it is non-toxic, and it's generally used in biological applications. Other rinsing agents known in the art are contemplated for use with embodiments.

This decellularization protocol has been shown to not disrupt fragile de novo ECM components secreted by the stem cells while being effective to remove stem cells from the engineered matrix. Following stem cell removal, this non-cellular bioscaffold can now be used for multiple applications (e.g., any cardiovascular application, wherein the approach is via surgical repair or reconstruction) in order to promote accelerated cardiovascular tissue regeneration, which without being bound by theory, the inventors believe will be driven by the presence of the species-matching de novo elastin that is contained within the engineered matrix of embodiments of the subject invention.

In certain embodiments, bioreactors can be used to apply mechanical forces on living cells (e.g., stem cells) and tissues (e.g., cardiovascular tissues) to induce a response that can be used for the benefit of tissue treatments (e.g., cardiovascular treatments.) Oscillatory fluid -induced shear stresses promote the heart valve phenotype (e.g., stem cells convert to heart valve -like cells).

The flow regimen may be quantified by a metric known as the OSI which the inventors have identified to operate in a specific, narrow range of physiological-relevance of: $0.18 <= OSI <= 0.23$ (noting OSI ranges from 0 with no flow oscillations and flow is uni-directional, to a maximum of 0.5 suggesting full temporal flow oscillations (see, e.g., Williams et. al., 2017). Following an experimental application of an OSI-regimen and its accompanying magnitudes of shear stress of physiological-relevance to 3-dimensional stem cell seeded substrates, it was surprisingly discovered that the constructs were filled with elastin, which had been thought extremely difficult if not impossible to generate in vitro. A process was then developed to safely remove the stem cells while leaving the newly generated elastin (e.g., of the same species as the species in whom the material is intended to be implanted) intact and undisrupted to form an improved surgical implant (e.g. human elastin implanted into a human host to repair or replace a cardiac, vascular or valvular defect.)

Embodiments are under assessment for somatic growth and function of a mitral valve replacement in juvenile baboons. Future applications may include subjecting biomaterials to an enhancement process so that they become elastin-rich and are yet acellular for subsequent implantation in any cardiovascular (e.g., cardiac patch, heart valve, or vascular graft) or non -cardiovascular (e.g., scar reduction, wound healing, cosmetic, general, hernia repair, orthopedic, sports medicine, or other) application that will utilize a surgical repair or reconstruction approach in which accelerated cardiovascular tissue regeneration is beneficial for a successful outcome.

In an embodiment, de novo elastin matrix is produced under physiologically-relevant OSI (e.g., $0.18 \leq OSI \leq 0.23$) and shear stress conditions (e.g., 3-9 dynes/cm$^2$), with the subsequent removal of cells (e.g., removal of the stem cells that produced the new elastin) via an optimized, safe, careful, decellularized protocol, using PSIS material as the underlying substrate.

The invention also contemplates alternative substrates, including but not necessarily limited to a non-woven mesh combination of poly-L-lysine (PLLA) and poly-glycolic acid (PGA). Any other scaffold that is biodegradable and allows for cell attachment and growth may be considered with the scope of certain embodiments of the subject invention (see, e.g., Rath et al., Differentiation and Distribution of Marrow Stem Cells in Flex-Flow Environments Demonstrate Support of the Valvular Phenotype, PLOS ONE, 2015 Nov 4;10(11); which is hereby incorporated herein by reference in its entirety). In addition, the applicability of the new elastin matrix without cellularity can serve several cardiovascular applications beyond heart valves that support somatic growth in young patients (e.g. vascular grafts, cardiac patches and heart valve substitutes with the capacity to regenerate host tissues after implantation), where accelerated regeneration may be beneficial.

Figure 1B:

Turning now to the figures, FIGS. 1A-1B show the careful removal of stem cells (decellularization) while leaving the engineered tissues or engineered extracellular matrix intact. FIG. 1A shows a tissue sample at 20× magnification before decellularization and FIG. 1B shows a tissue sample at 20× magnification after decellularization.

Figure 2A:
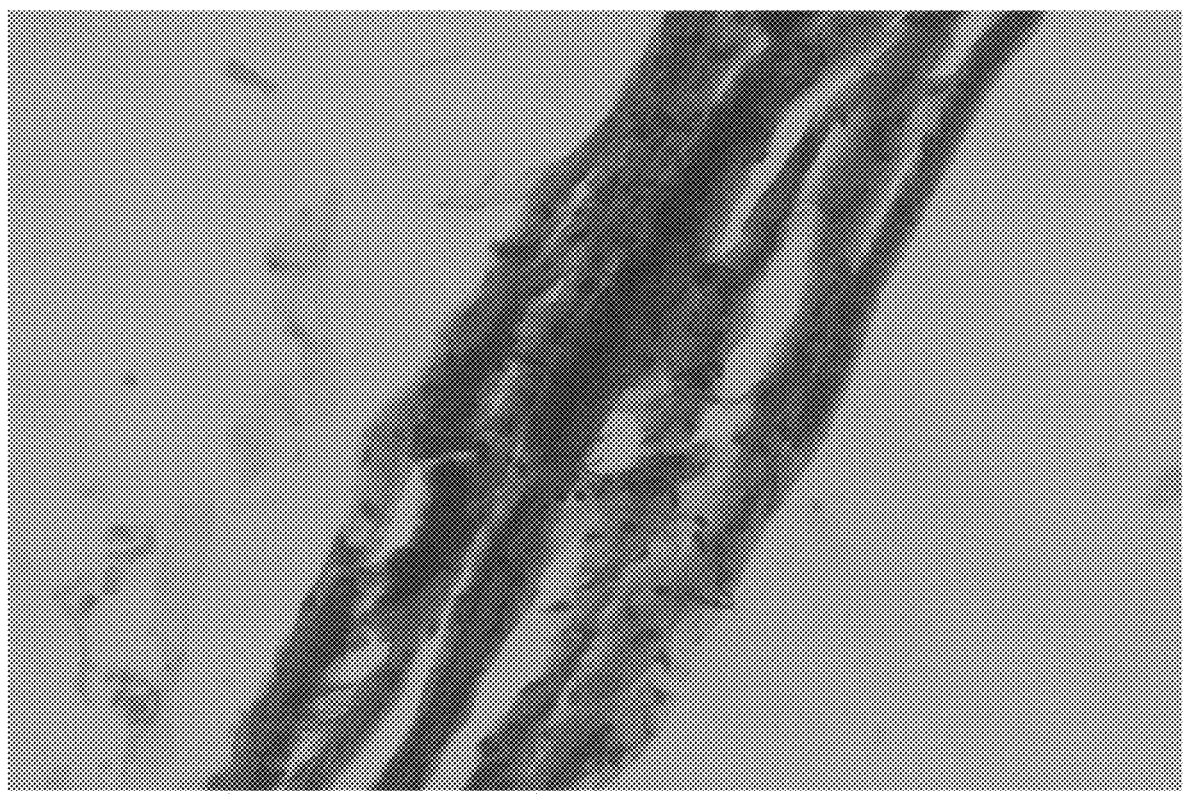
FIGS. 2A-2C show porcine small intestinal submucosa strips stained with Movat's on (2A) raw decellularized, (2B) 12 hours careful re-decellularized, and (2C) 24 hours careful re-decellularized bioscaffold.
Figure 2B:
Figure 2C:
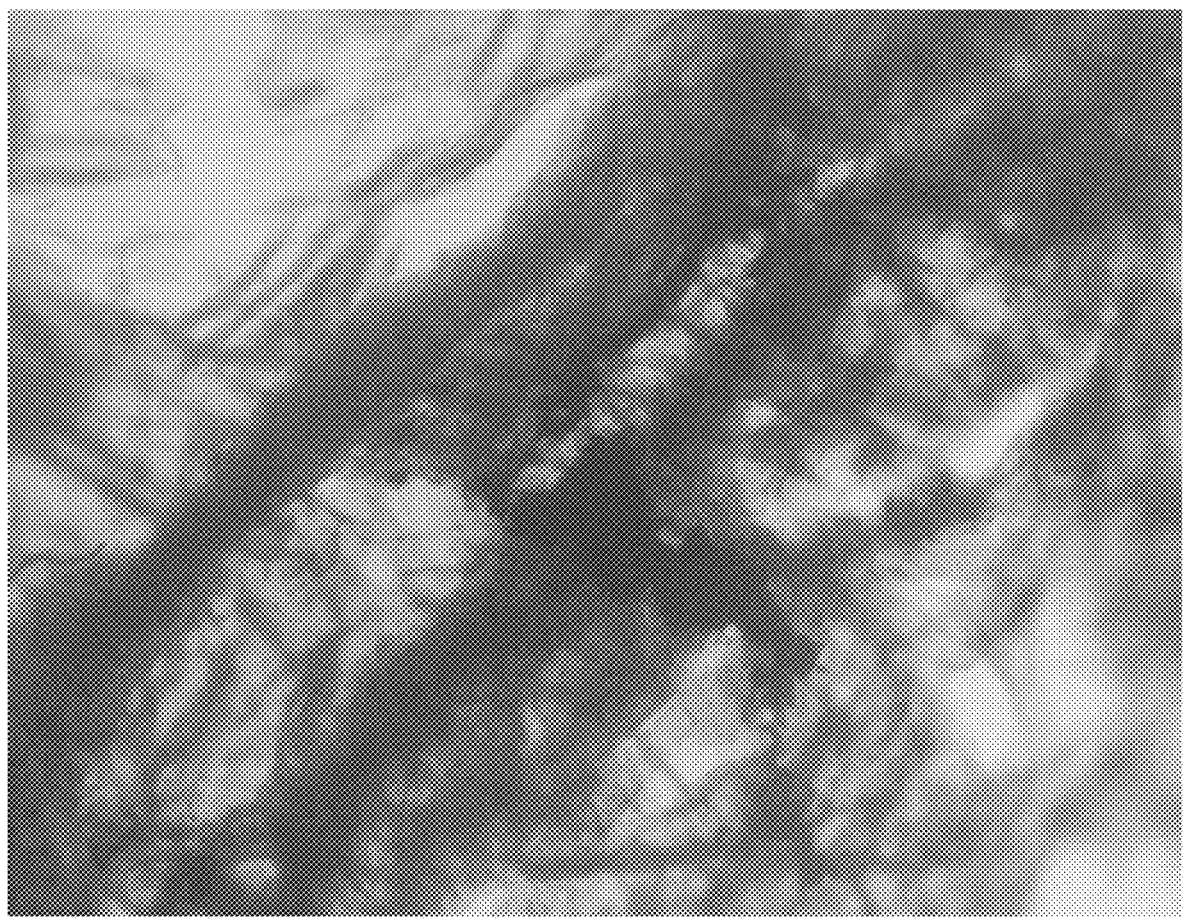

FIGS. 2A-2C show 20× magnification of porcine small intestinal submucosa strips stained with Movat's on (2A) raw decellularized PSIS bioscaffold, (2B) 12 hours careful re -decellularized, and (2C) 24 hours careful re-decellularized bioscaffold.

Figure 3A:
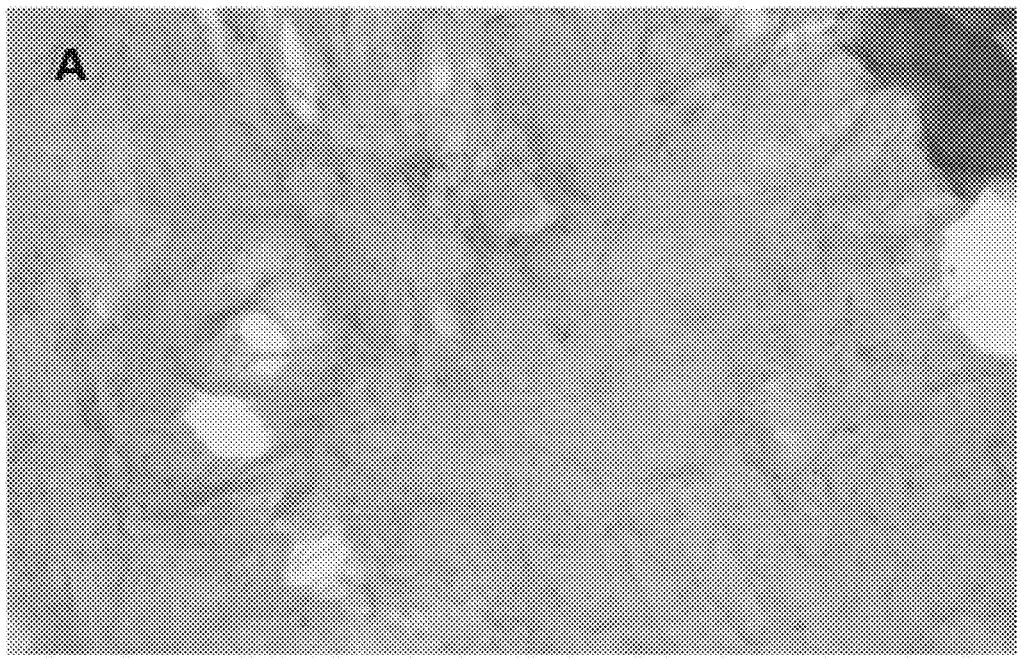
FIGS. 3A-3B show porcine small intestinal submucosa (3A) raw decellularized and (3B) explant of baboon 11 months post-implantation. H&E histological stains show (3A) cells remaining on the raw scaffold pre-implantation and (3B) a chronic immune response 11 months post-implantation.
Figure 3B:
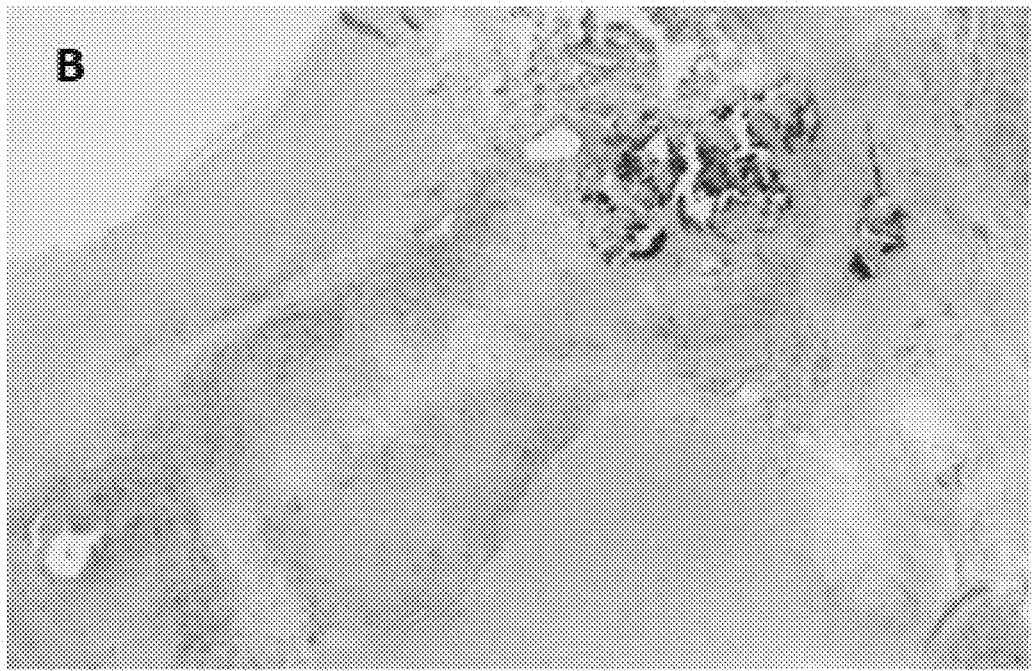

FIGS. 3A-3B show porcine small intestinal submucosa (3A) 10× magnification of raw decellularized and (3B) 4× magnification of explant of baboon 11 months post-implantation. H&E histological stains show (3A) cells remaining on the raw scaffold pre-implantation and (3B) a chronic immune response 11 months post-implantation.

Figure 4:
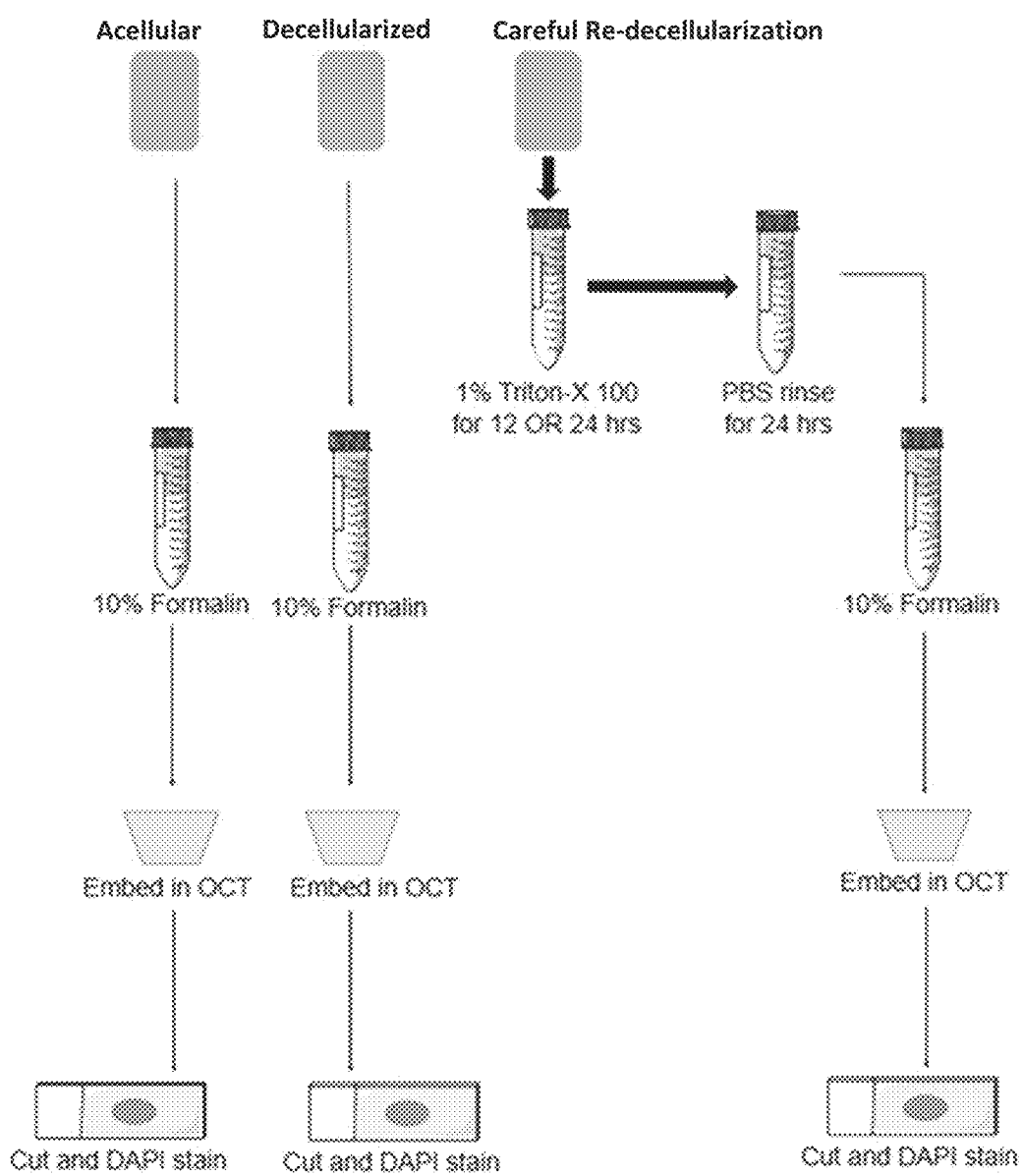
FIG. 4 shows a procedure for preparing slides from porcine small intestinal submucosa strips.

FIG. 4 shows a procedure for preparing slides from porcine small intestinal submucosa strips.

Figure 5A:
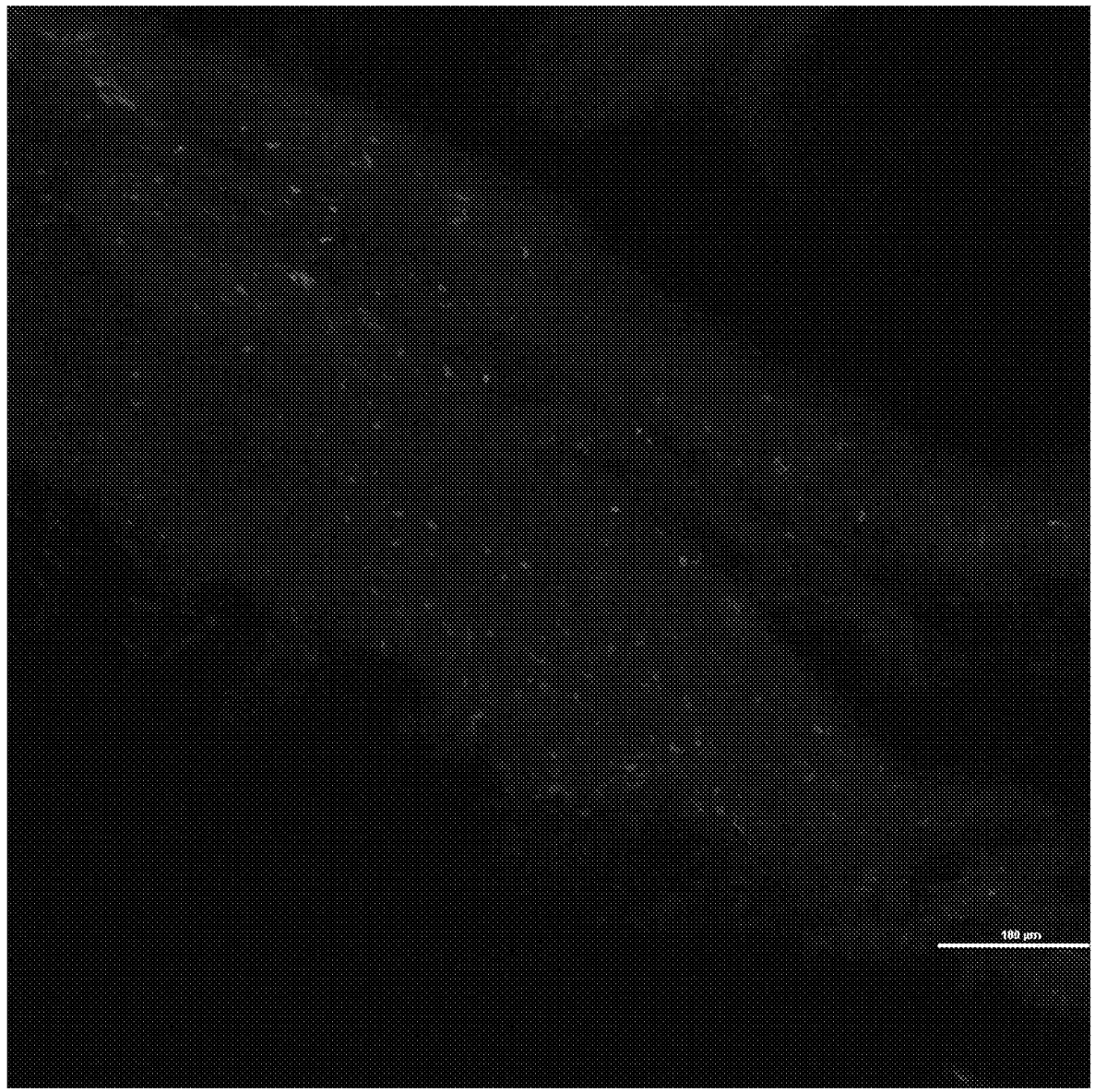
FIGS. 5A-5F show PSIS strips stained with DAPI on (5A) acellular, (5C) decellularized, and (5E) careful re-decellularized bioscaffolds; and number of cells counted on (5B) acellular, (5D) decellularized, and (5F) careful re-decellularized bioscaffolds. The scale bars in FIGS. 5A, 5C, and 5E are 100 μm; and the scale in FIGS. 5B, 5D, and 5F correspond to that in FIGS. 5A, 5C, and 5E, respectively.
Figure 5B:
Figure 5C:
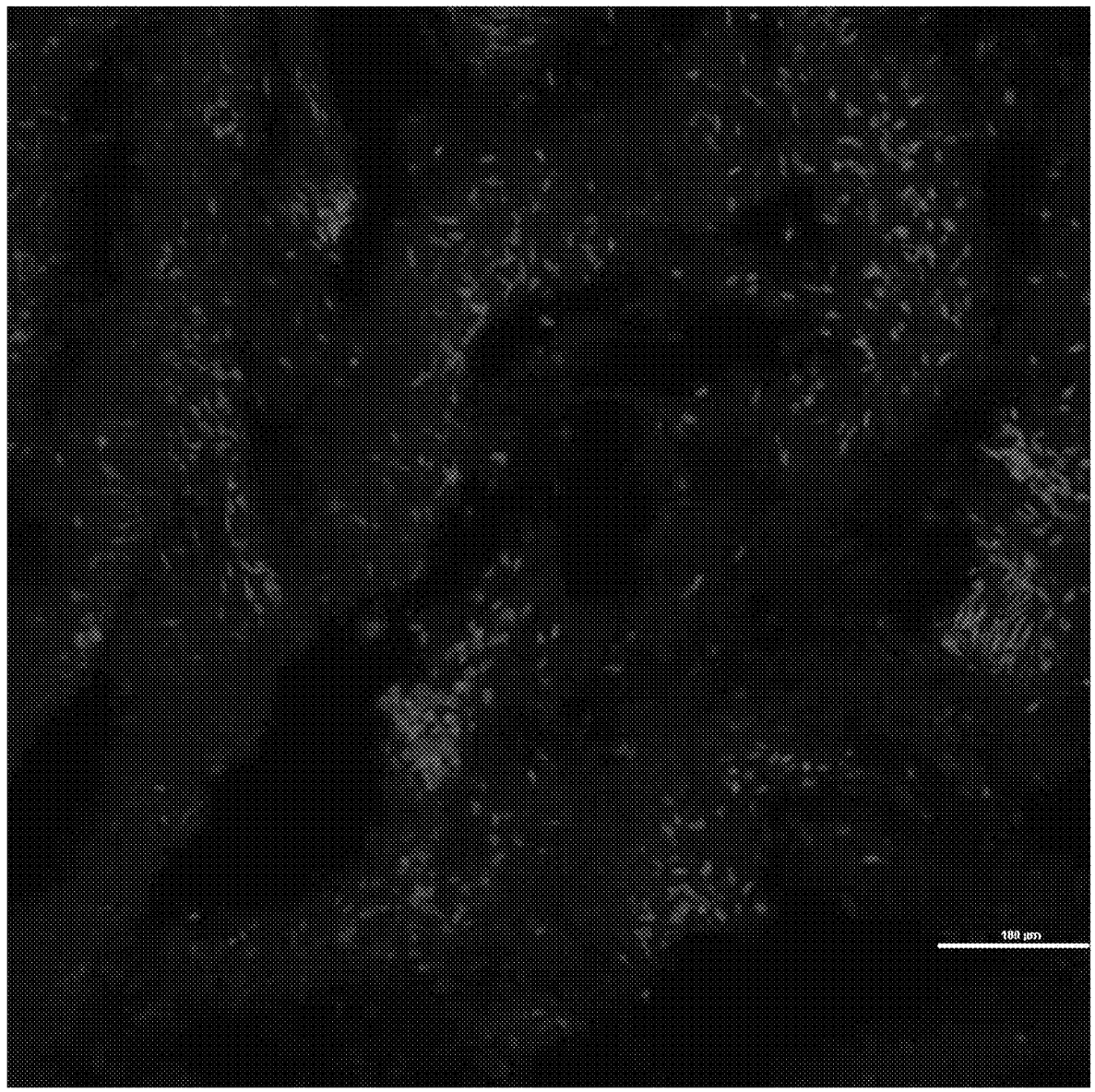
Figure 5D:
Figure 5E:
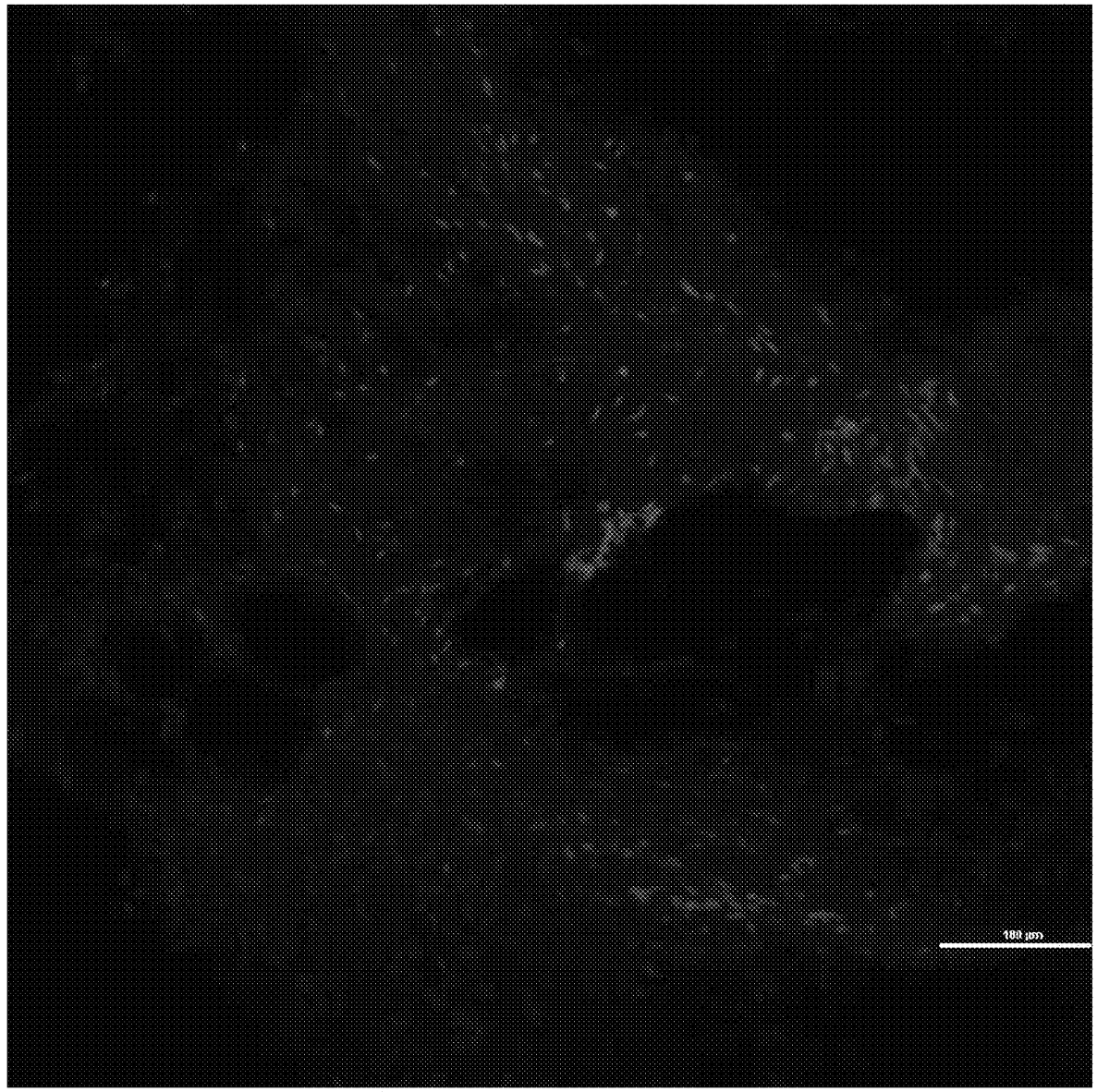
Figure 5F:
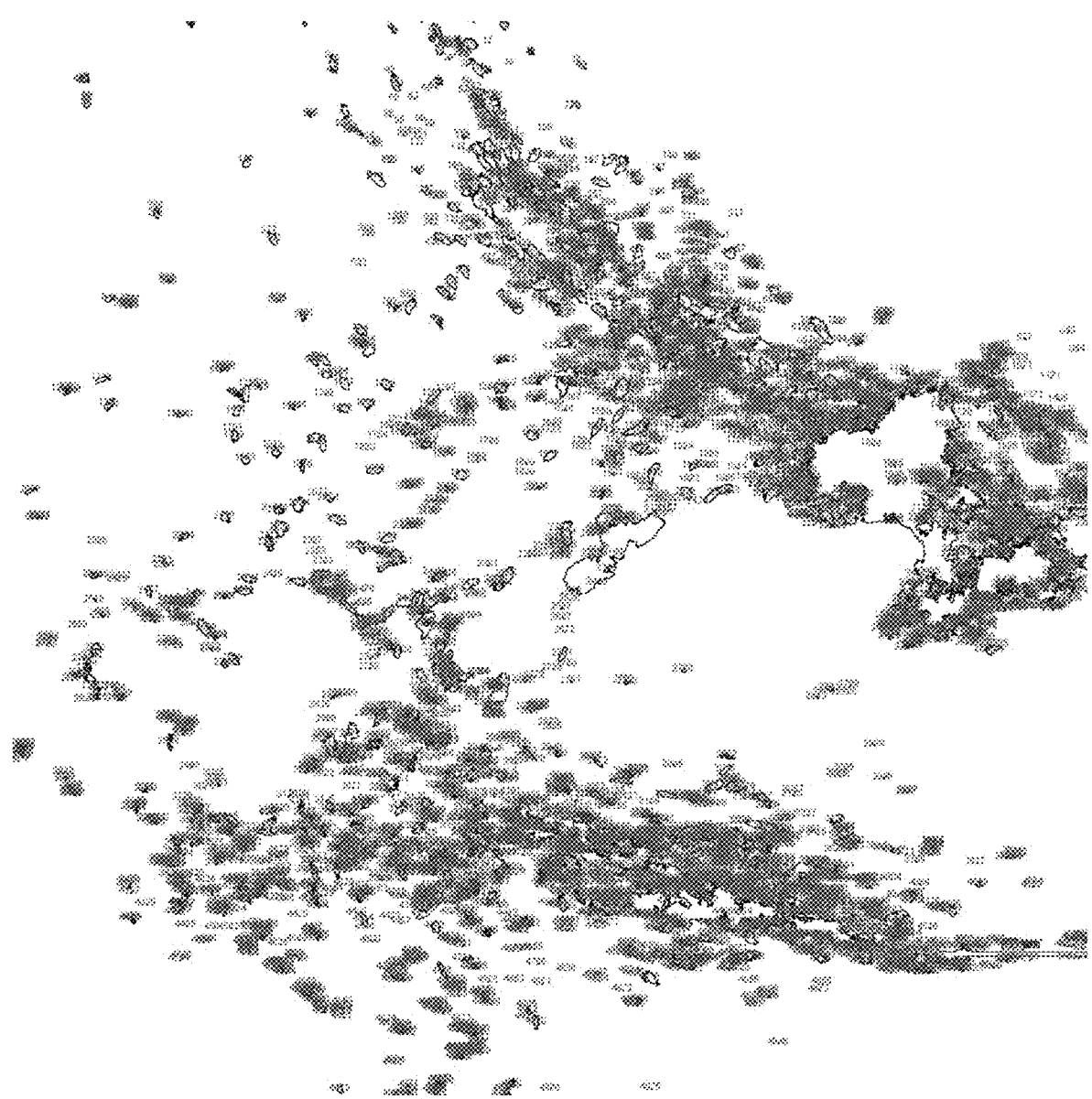
Figure 6A:
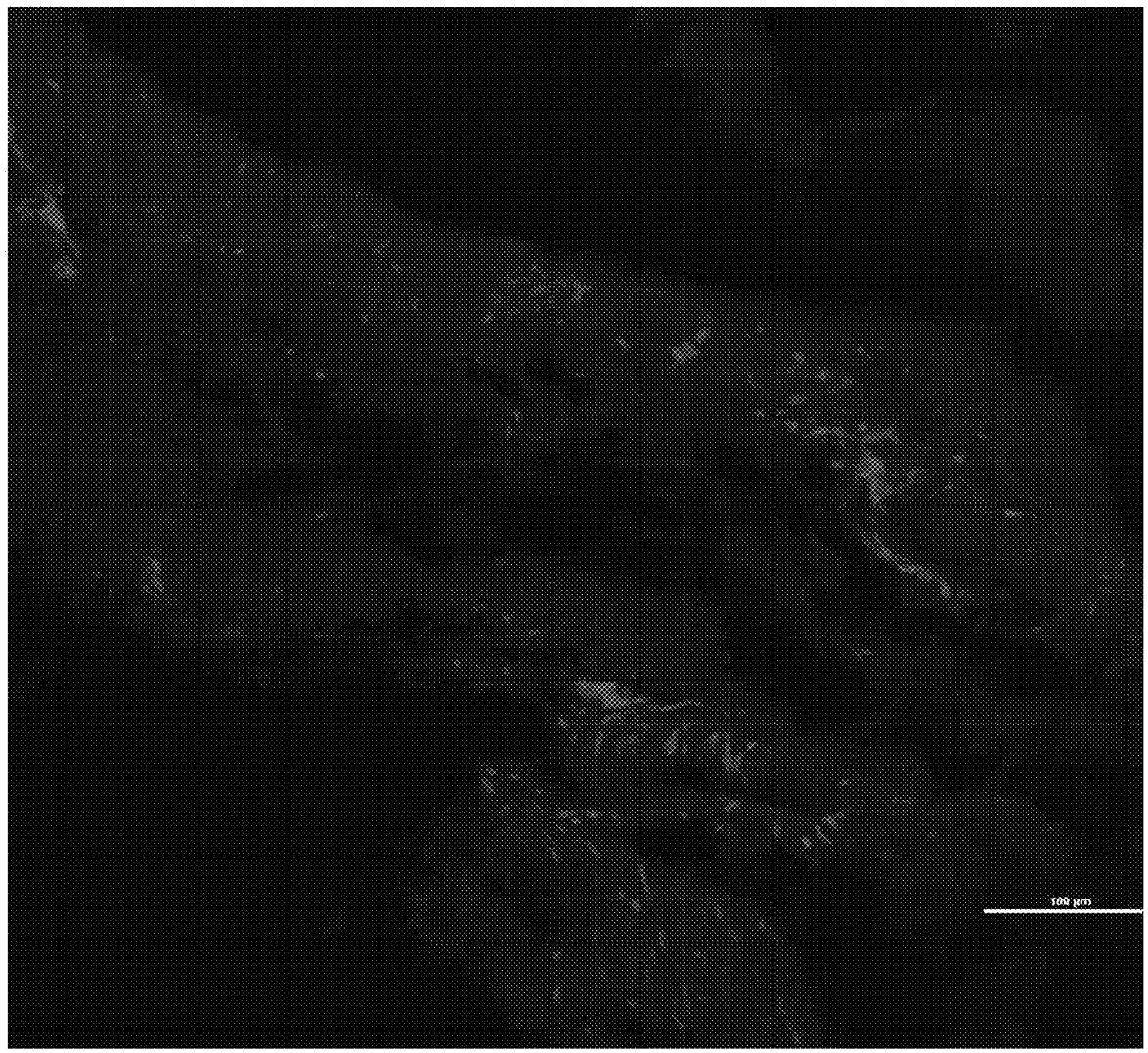
FIGS. 6A-6H shows porcine small intestinal submucosa strips stained with DAPI on (6A) acellular, (6C) decellularized, (6E) 12 hour and (6G) 24 our re-decellularized bioscaffolds. Images of cells (6B, 6D, 6F, 6H) counted on each bioscaffold, respectively. The scale bars in FIGS. 6A, 6C, 6E, and 6G are 100 μm; and the scale in FIGS. 6B, 6D, 6F, and 6H correspond to that in FIGS. 6A, 6C, 6E, and 6G, respectively.
Figure 6B:
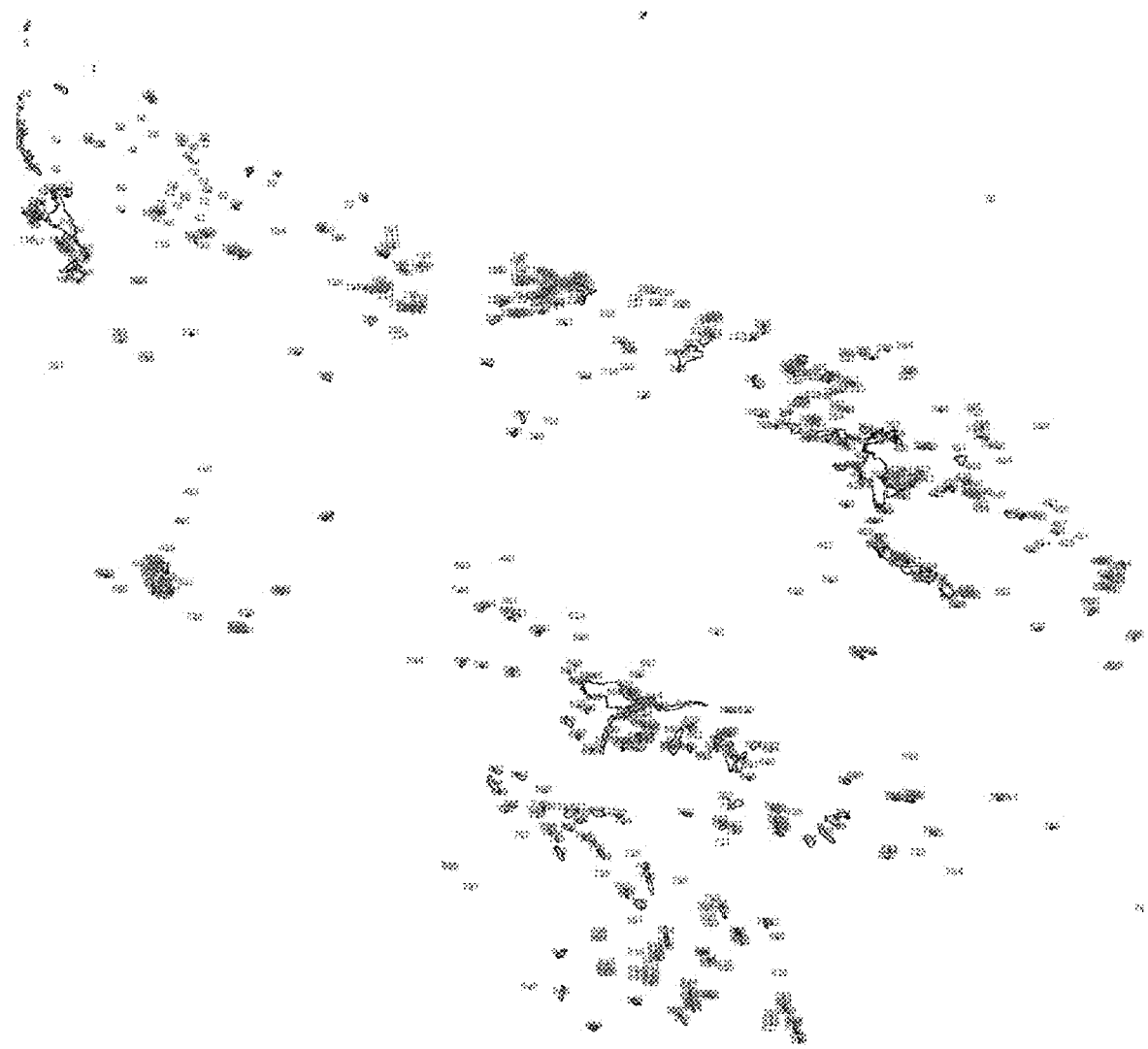
Figure 6C:
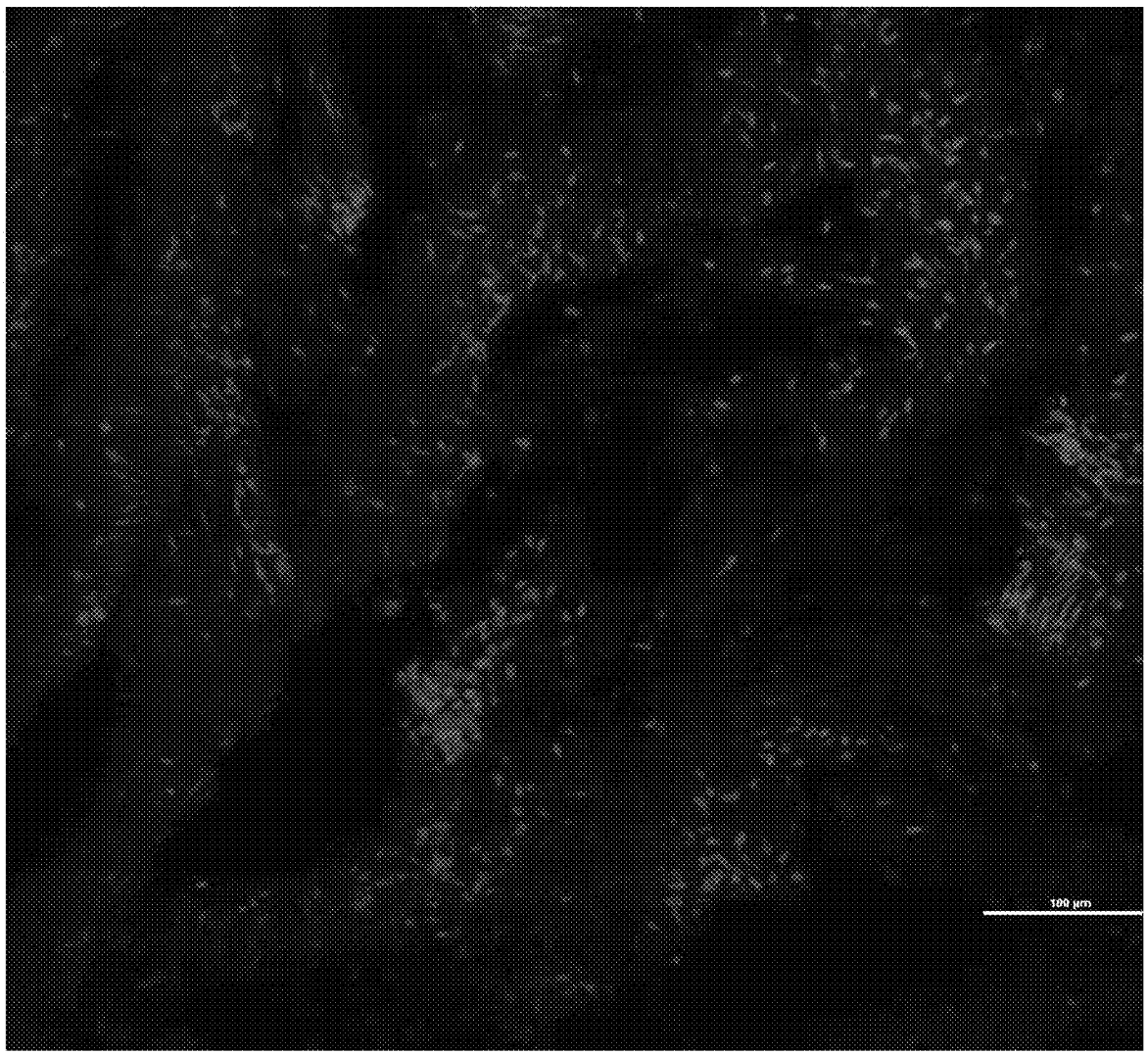
Figure 6D:
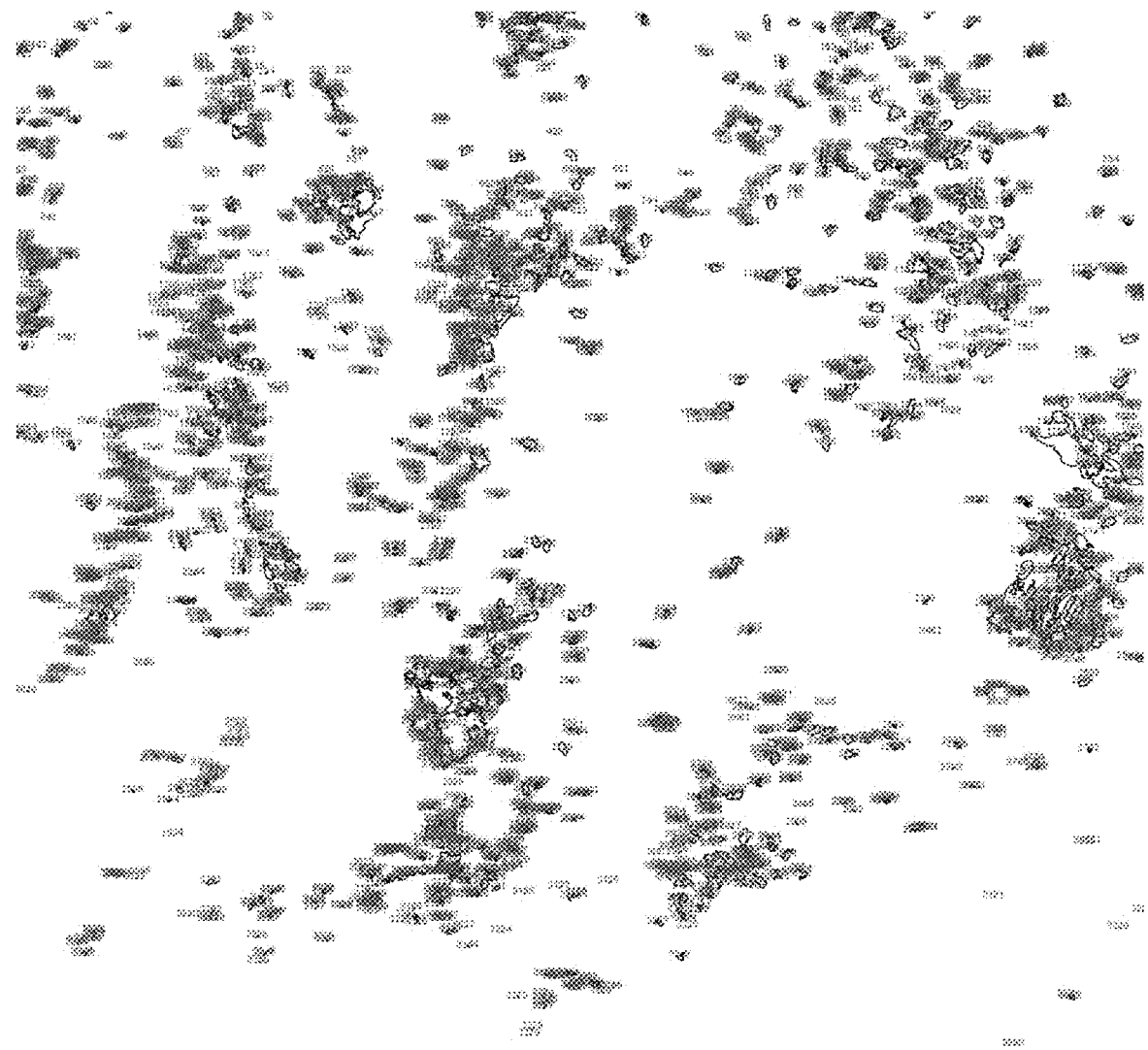
Figure 6E:
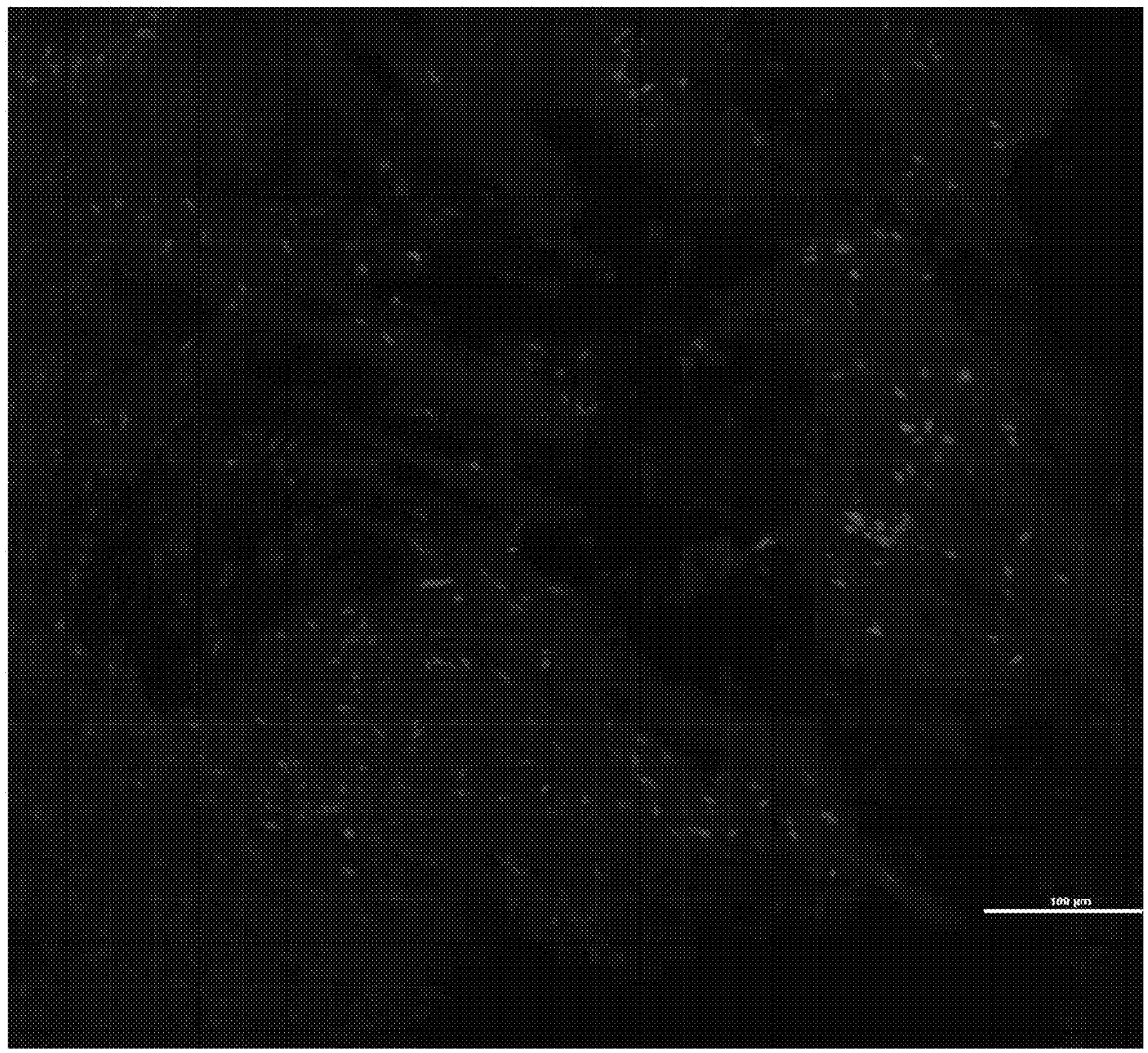
Figure 6F:
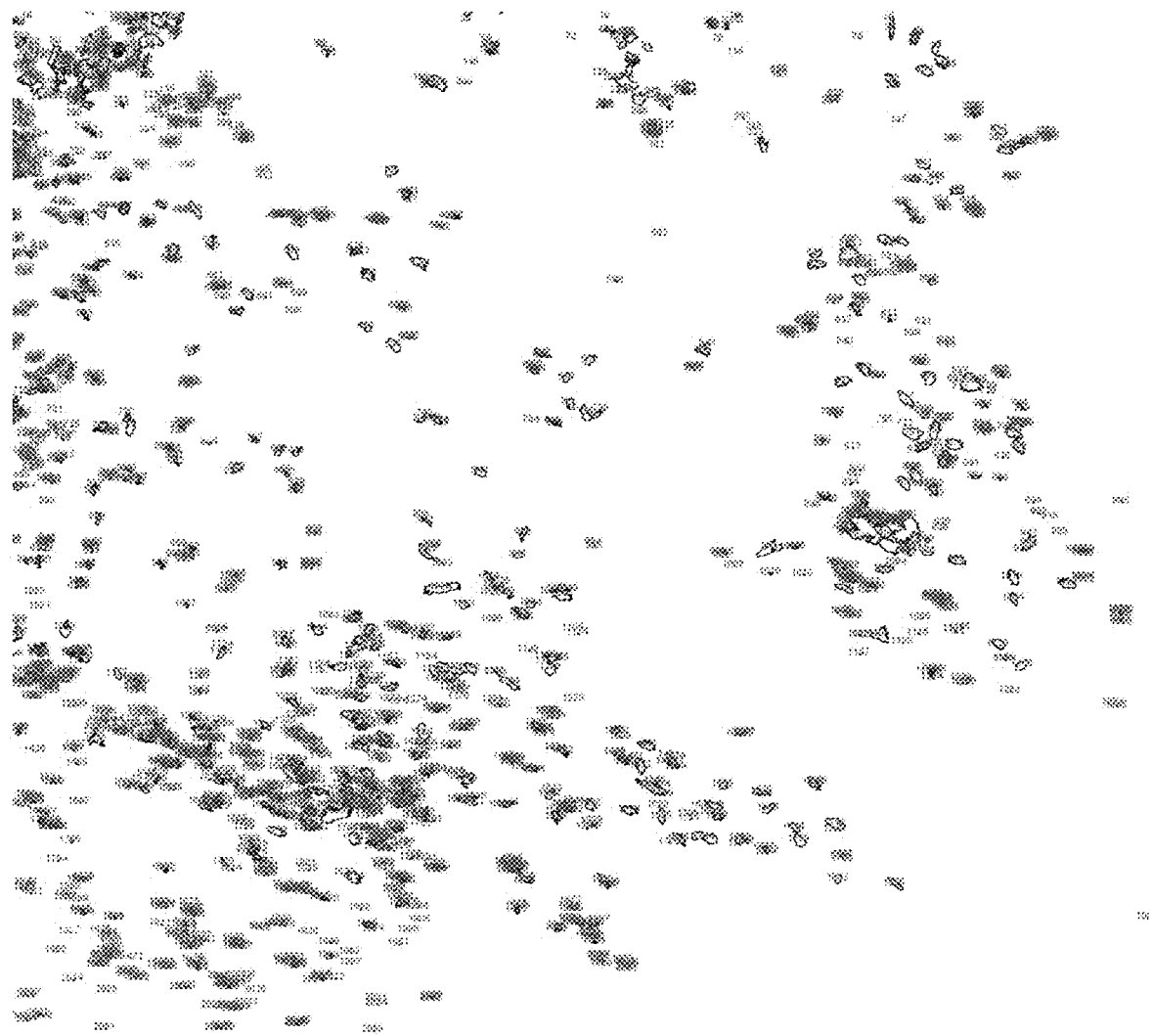
Figure 6G:
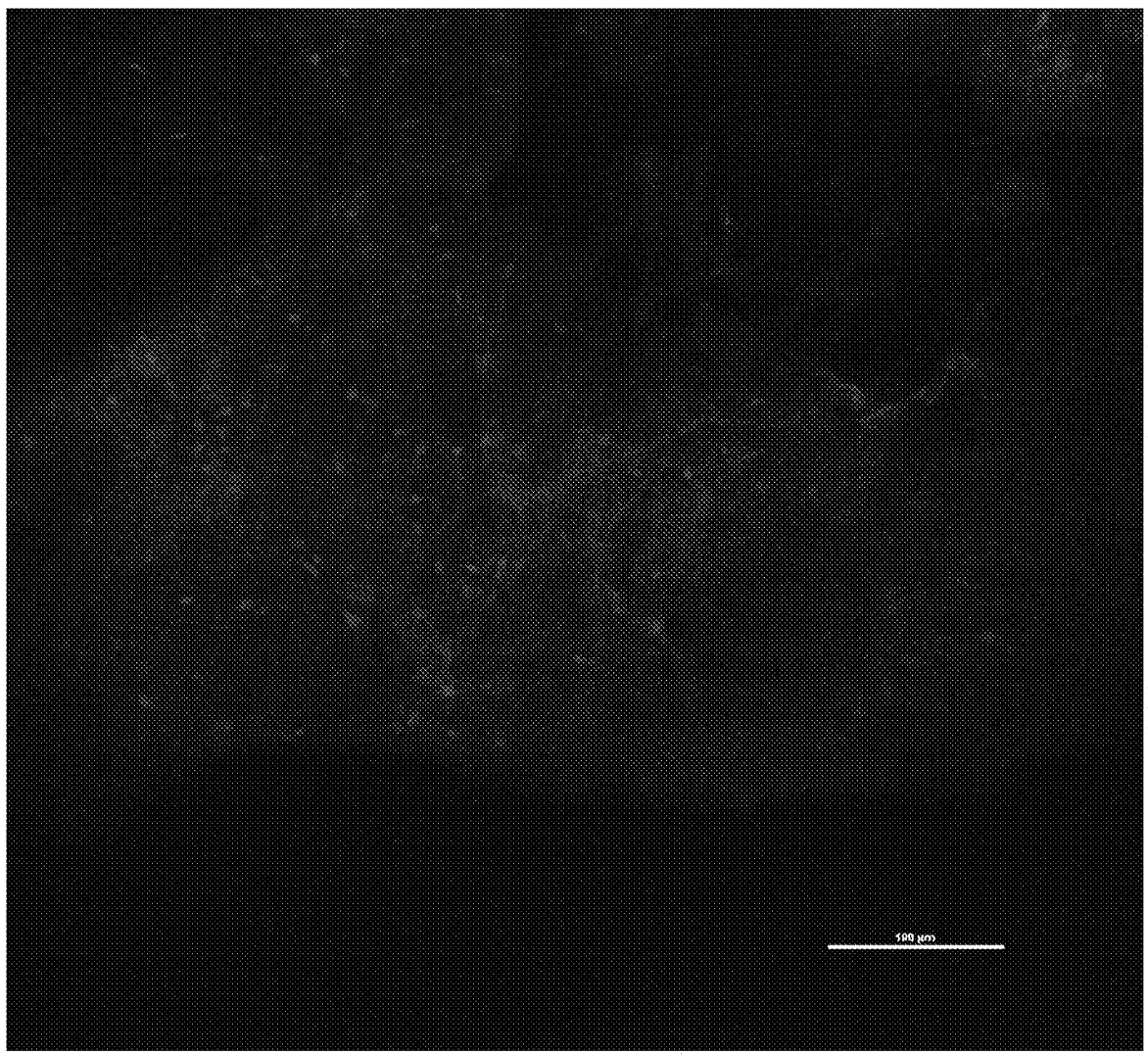
Figure 6H:
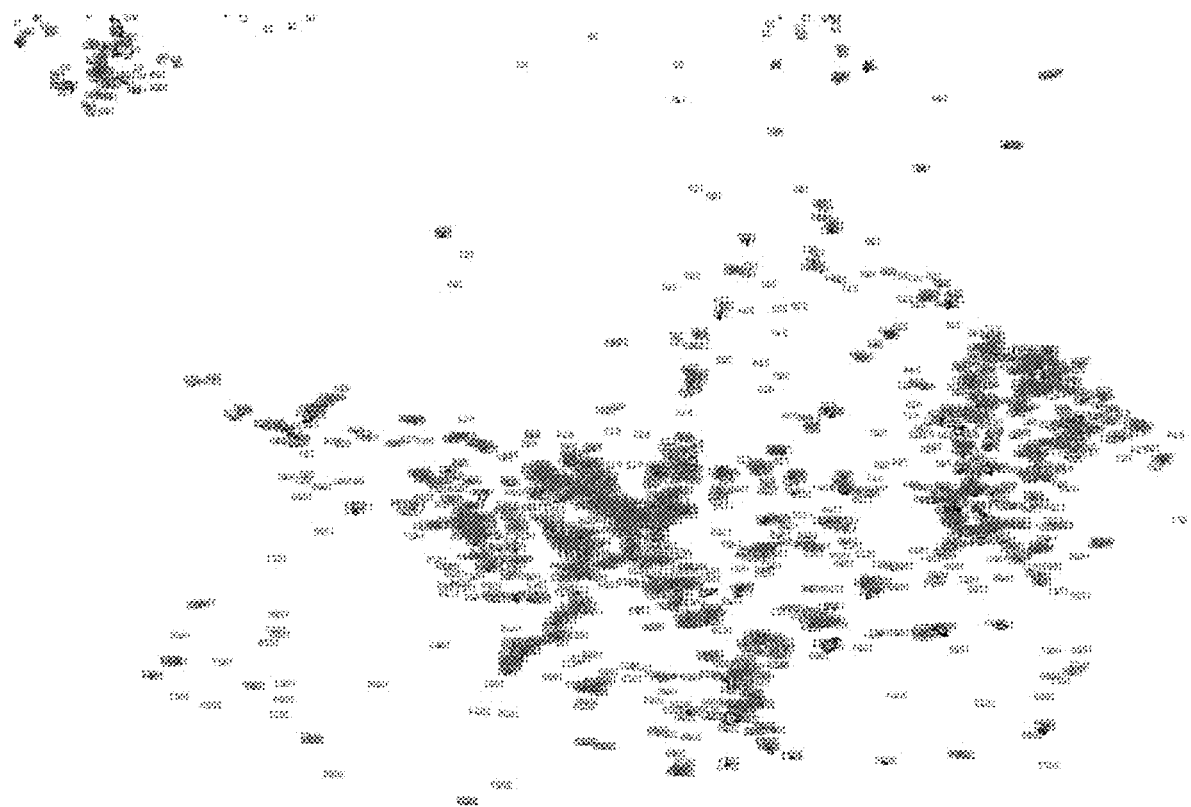

FIGS. 5A-5F show PSIS strips stained with DAPI on (5A) acellular, (5C) decellularized, and (5E) careful re-decellularized bioscaffolds; and number of cells counted on (5B) acellular, (5D) decellularized, and (5F) careful re-decellularized bioscaffolds. The scale bars in FIGS. 5A, 5C, and 5E are 100 μm; and the scale in FIGS. 5B, 5D, and 5F correspond to that in FIGS. 5A, 5C, and 5E, respectively.

FIGS. 6A-6H shows porcine small intestinal submucosa strips stained with DAPI on (6A) acellular, (6C) decellularized, (6E) 12 hour and (6G) 24 our re-decellularized bioscaffolds. Images of cells (6B, 6D, 6F, 6H) counted on each bioscaffold, respectively. The scale bars in FIGS. 6A, 6C, 6E, and 6G are 100 μm; and the scale in FIGS. 6B, 6D, 6F, and 6H correspond to that in FIGS. 6A, 6C, 6E, and 6G, respectively.

Figure 7:
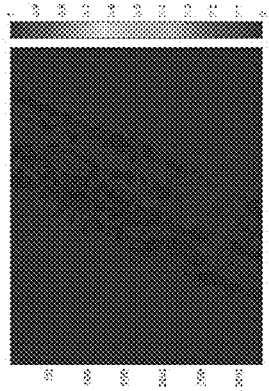
FIG. 7 shows elastin comparison effects of decellularization on a raw Bio-scaffold.
Figure 7:
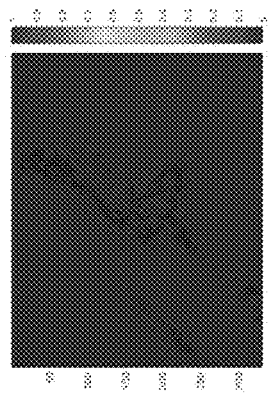
Figure 7:
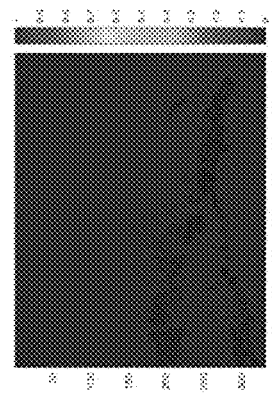
Figure 7:
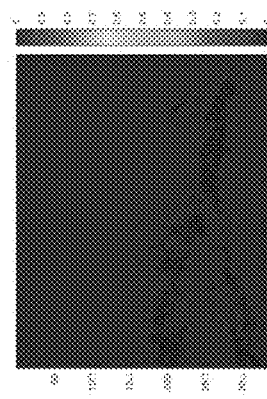
Figure 7:
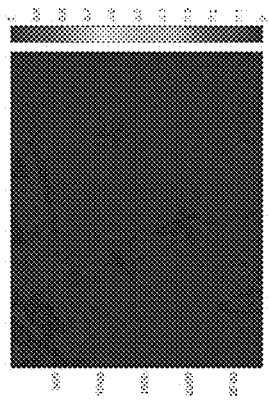
Figure 7:
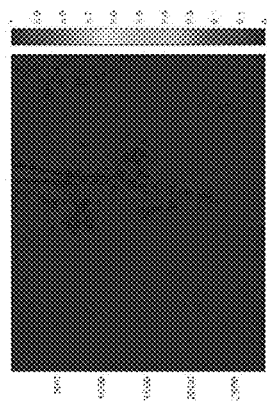
Figure 7:
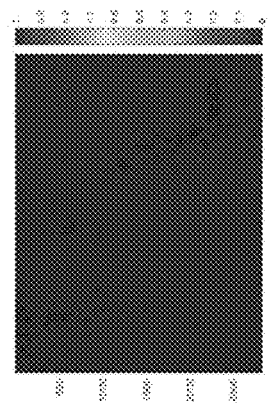

FIG. 7 shows elastin comparison effects of decellularization on a raw Bio-scaffold for three different processing protocols: 12 hr. Decellularization (3 images), 24 hr. Decellularization (3 images), and DC Control (Ver. 1) (1 image), respectively.

Figure 8:
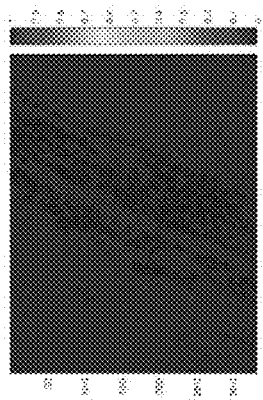
FIG. 8 shows collagen comparison effects of decellularization on a raw Bio-scaffold.
Figure 8:
Figure 8:
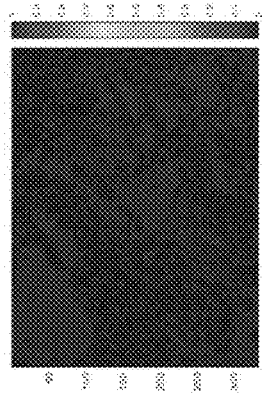
Figure 8:
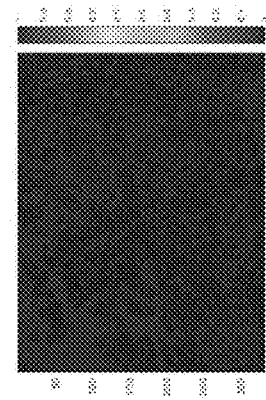
Figure 8:
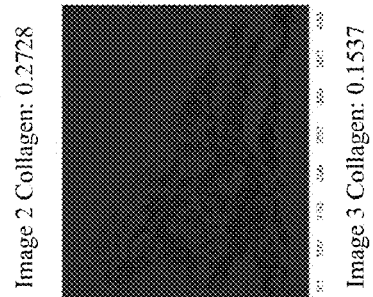
Figure 8:
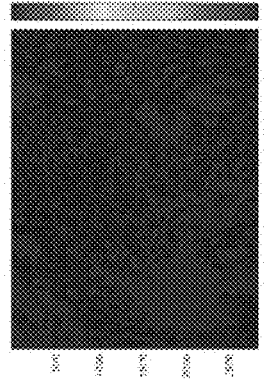
Figure 8:
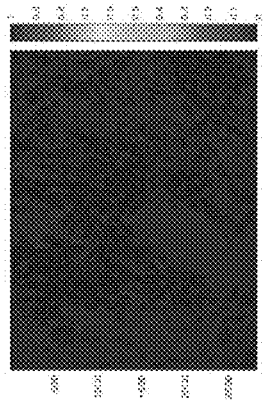
Figure 8:
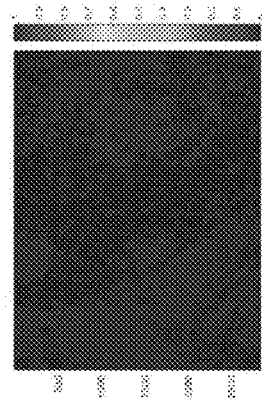

FIG. 8 shows collagen comparison effects of decellularization on a raw Bio-scaffold for three different processing protocols: 12 hr. Decellularization (3 images), 24 hr. Decellularization (3 images), and DC Control (Ver. 1) (1 image), respectively.

FIGS. 7 and 8 are spatial intensity maps for elastin and collagen, respectively. Images represent elastin (FIG. 7) and collagen (FIG. 8) levels, respectively, for the control and the two decellularization time points (12 hours and 24 hours) illustrating the decellularization protocol effects the ECM structure. It is equally important for the process to be able to remove the cellular content from the bioscaffold and to simultaneously maintain the ECM structure so that the bioscaffold retains its function.

These spatial intensity maps were obtained by doing image processing via a combination of ImageJ and an in-house MATLAB script. The bioscaffolds were first stained with a histological stain called Movat's, where different ECM structures can be distinguished. Elastin is stained in a black-purple color, while collagen is stained in a yellow-green color. The images were normalized, based off the control bioscaffold, and the color intensities of the components were used to quantify the percentage of ECM components present at each section of the bioscaffold. The DC control (Ver. 1) in FIGS. 7 and 8 correspond to FIG. 2A. Image 1 of the 12 hr. Decellularization in FIGS. 7 and 8 corresponds to FIG. 2B. Image 1 of the 24 hr. decellularization in FIGS. 7 and 8 corresponds to FIG. 2C. Images 2 and 3 of FIGS. 7 and 8 for both time points of decellularization are other bioscaffold samples that underwent the same process.

Figure 9:
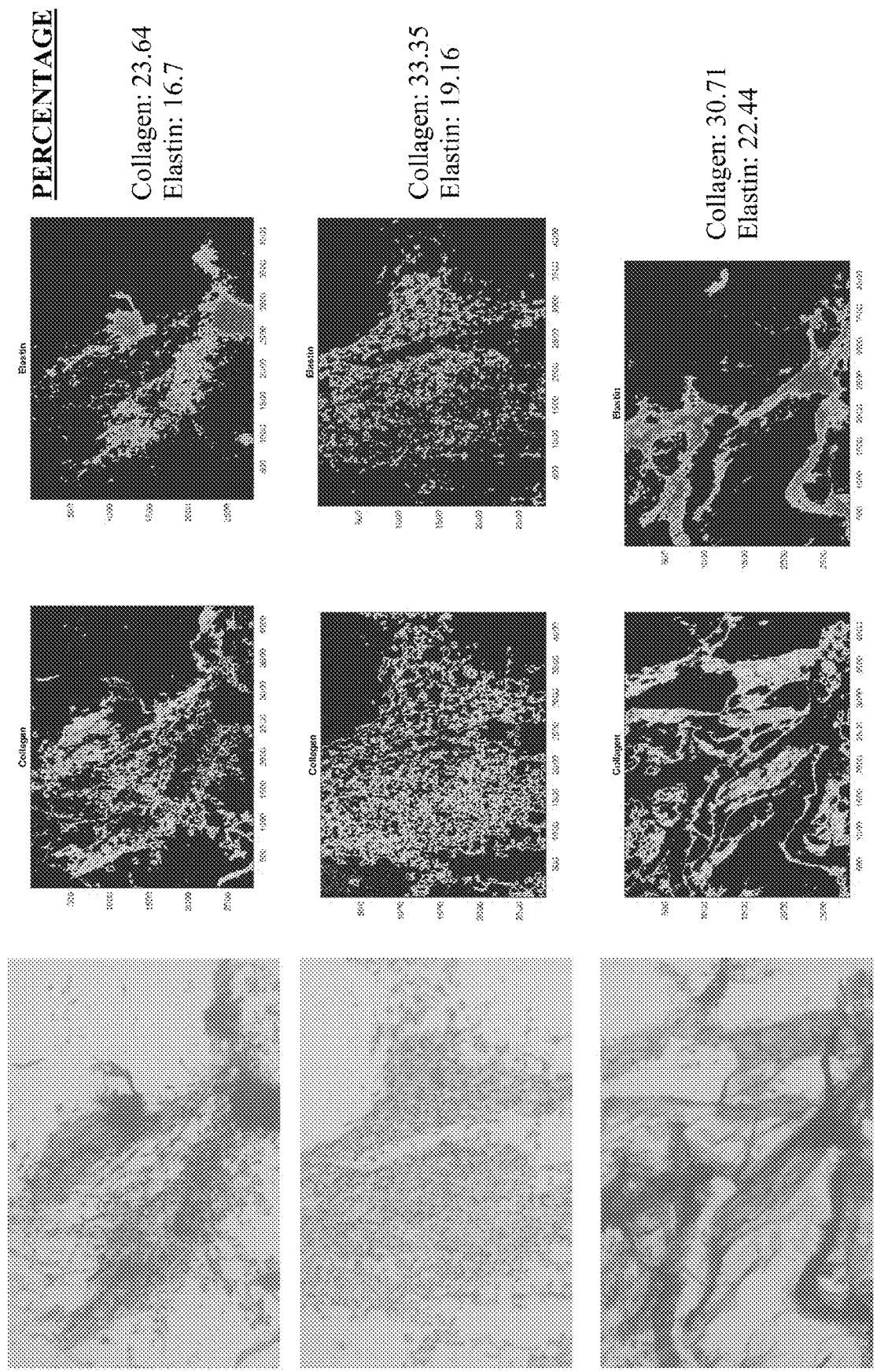
FIG. 9 shows collagen and elastin percentage on untreated engineered tissues in the Control Group.

FIG. 9 shows collagen and elastin percentage on untreated engineered tissues in the Control Group.

Figure 10:
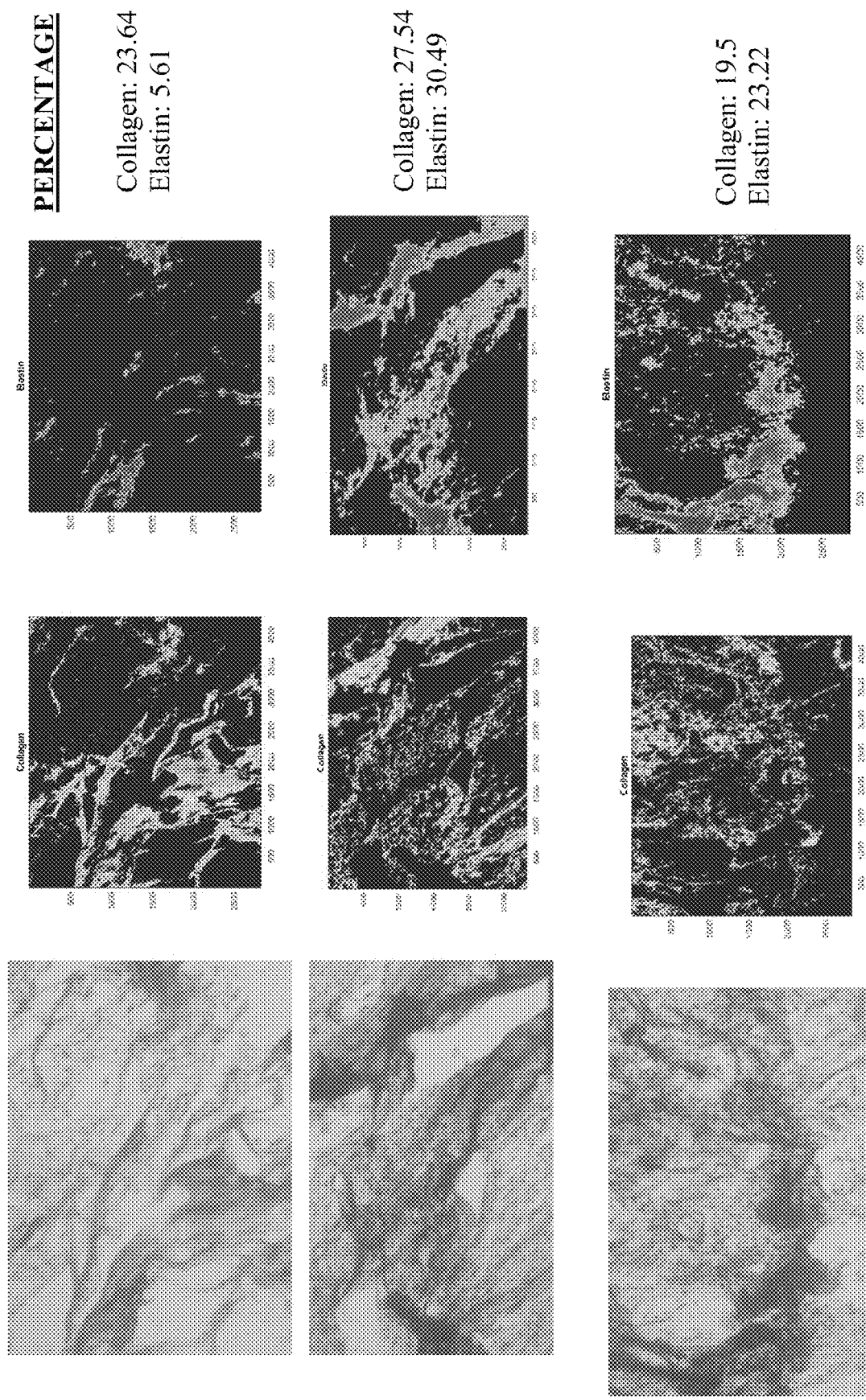
FIG. 10 shows collagen and elastin percentage on untreated engineered tissues in the Control Group.

FIG. 10 shows collagen and elastin percentage on untreated engineered tissues in the Control Group.

Figure 11:
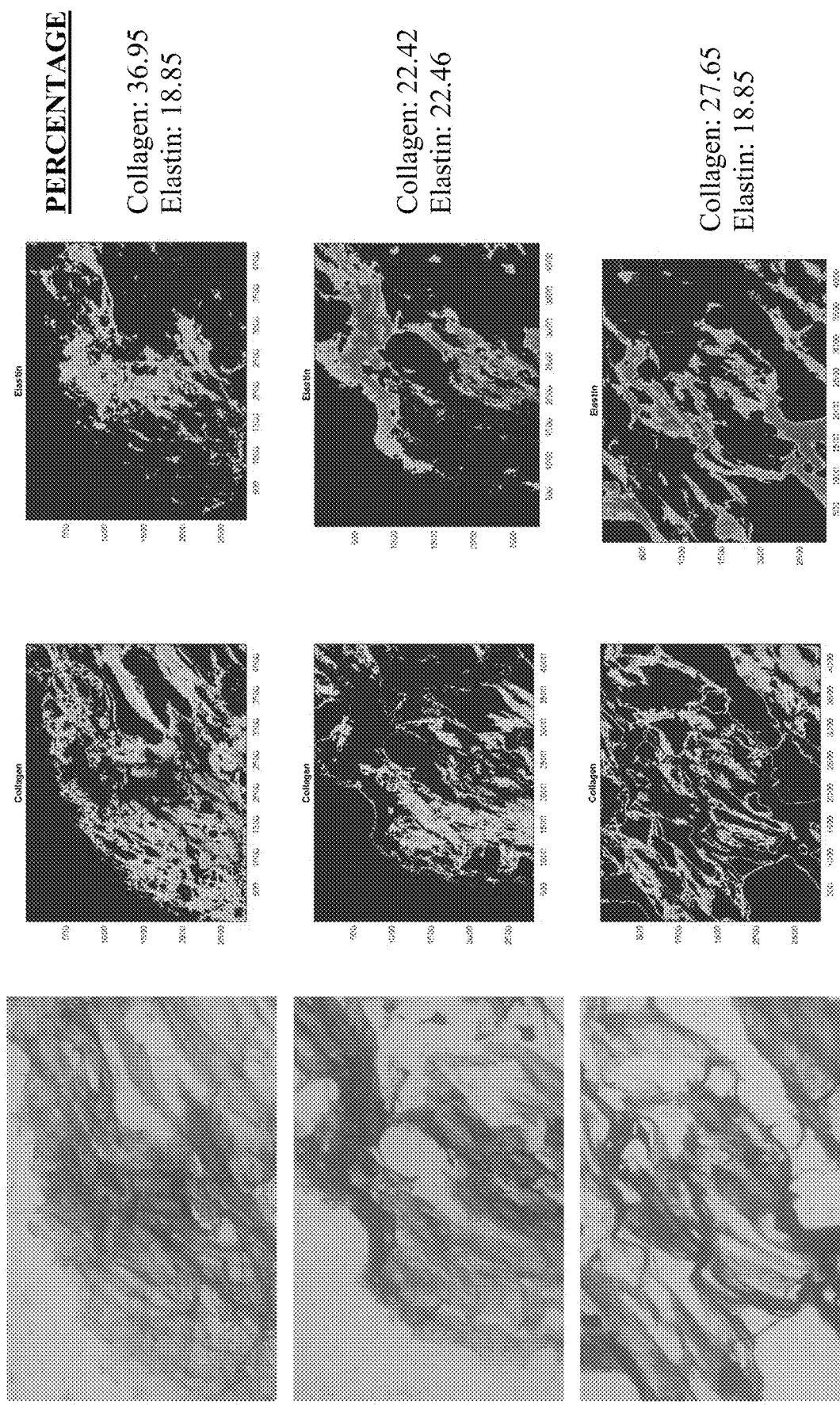
FIG. 11 shows collagen and elastin percentage on decellularized engineered tissues in the TX100 Group.

FIG. 11 shows collagen and elastin percentage on decellularized engineered tissues in the TX100 Group.

Figure 12:
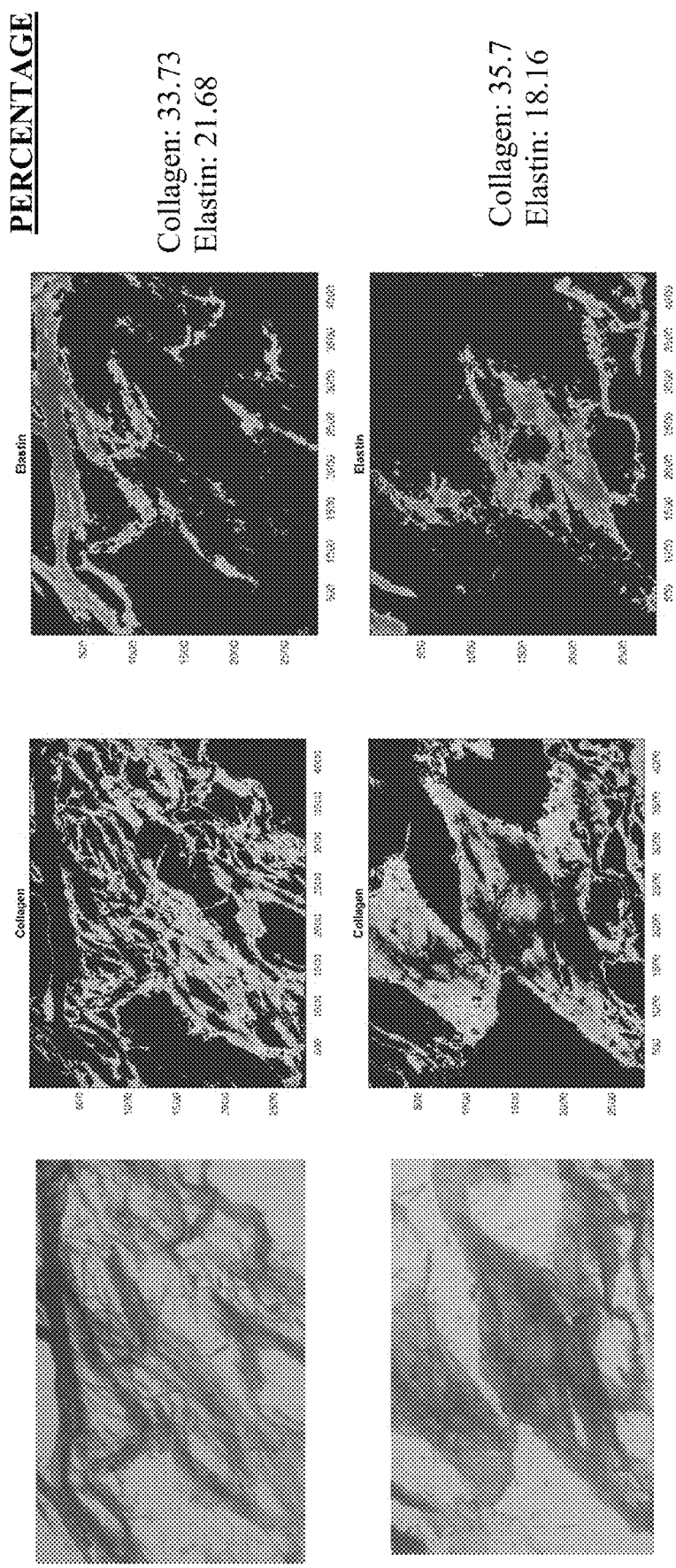
FIG. 12 shows collagen and elastin percentage on decellularized engineered tissues in the TX100 Group.

FIG. 12 shows collagen and elastin percentage on decellularized engineered tissues in the TX100 Group.

FIGS. 9-12 are spatial intensity maps obtained from our histological Movat's stains, similar to FIGS. 7 and 8. However, these PSIS bioscaffold were seeded with human bone marrow stem cells (7 million cells/bioscaffold) in rotisserie culture for 8 days. FIGS. 9-10 demonstrate the ECM structures, with spatial intensity maps showing the percentage of collagen and elastin, as well as the attachment of the seeded stem cells.

FIGS. 11 and 12 are PSIS bioscaffolds that were seeded with stem cell, similar to FIGS. 9-10, but with the decellularization protocol being applied to these bioscaffolds. The decellularization protocol consisted of treatment in 1% TX100 in DI water, agitated on a shaker set at 20 RPM for 24 hours at room temperature. The samples were then washed with PBS for 24 hours at room temperature, with a replacement of fresh PBS at the 12-hour mark. Comparing FIGS. 9-10 to FIGS. 11-12, it is demonstrated that the decellularization protocol can safely remove the cells from the bioscaffold as well as maintain the ECM structures of collagen and elastin. Both of these objectives are crucial to clinical success of the scaffold.

FIG. 13 shows the design and results of a computational fluid dynamics (CFD) analysis of an in-house torpedo bioreactor design with a waveform applied having a 17% forward and 83% backwards flow, which provided an OSI of ~0.20 and time averaged wall shear stress (TAWSS) of ~3.1 dynes/cm2, both within the ranges that are acceptable for proper tissue ECM growth.

FIGS. 14A-14E show outcomes of a version 1 torpedo bioreactor.

FIGS. 15A-15E show outcomes of a version 2 torpedo bioreactor.

Figures 14A, 14B, 14C, 14D, 14E:
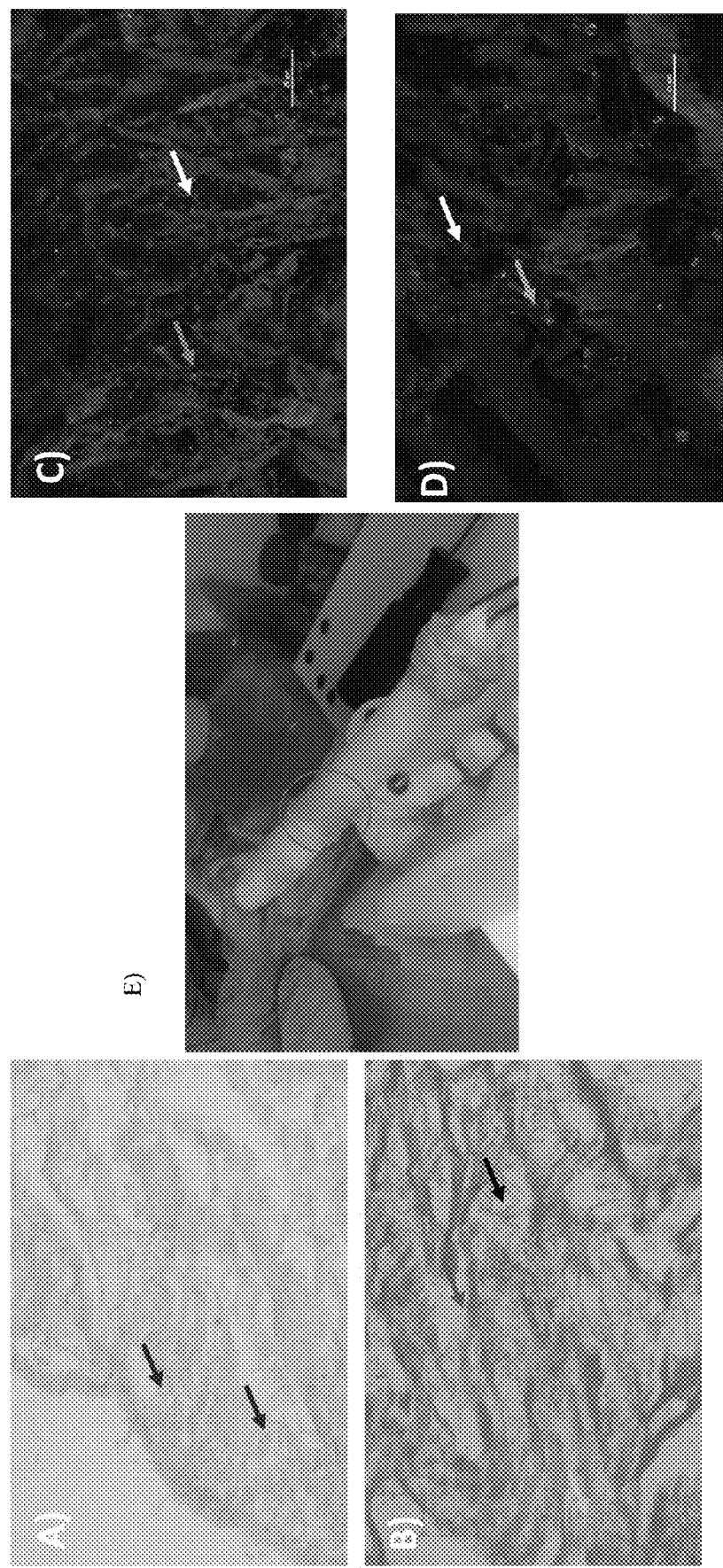
FIGS. 14A-14E show outcomes of a version 1 torpedo bioreactor.
Figures 15A, 15B, 15C, 15D, 15E:
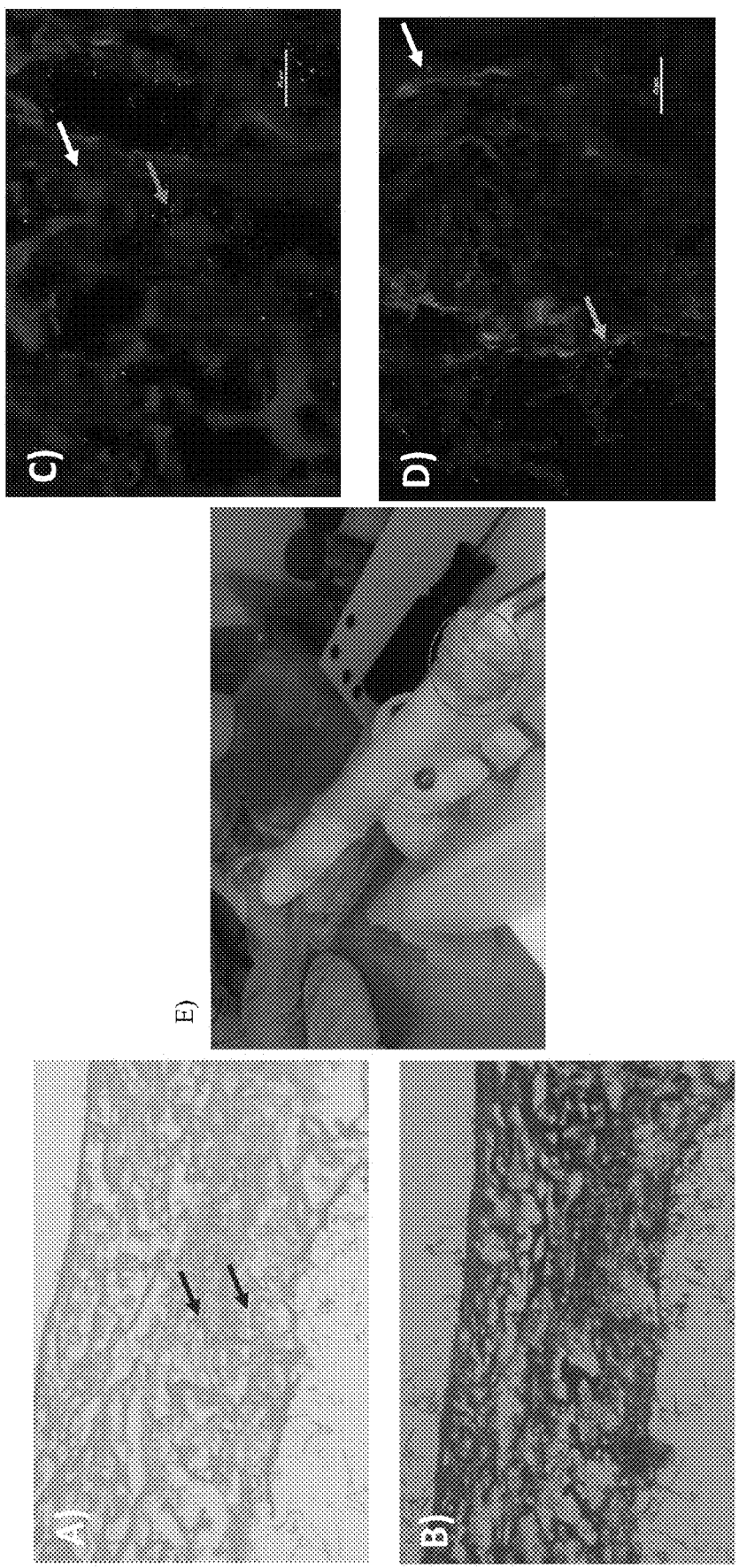
FIGS. 15A-15E show outcomes of a version 2 torpedo bioreactor.

FIGS. 14 and 15 are demonstrating the two PSIS valves the were seeded with stem cells and exposed to a waveform (e.g., as described for FIG. 13) in the torpedo bioreactor to allow for proper ECM growth (FIGS. 14E and 15E). FIGS. 14A and 15A are H&E images showing the morphology of the tissue as well as the ability of the cells (depicted by blue arrows) to attach and remain on the PSIS bioscaffold. FIGS. 14B and 15B demonstrate the ECM components of collagen (depicted as yellow-red arrows) and elastin (depicted as black arrows), respectively, via a histological Movat's stain to distinguish ECM components. FIGS. 14C, 14D, 15C, and 15D show that the stem cells, when exposed to the specified waveform in the torpedo bioreactor, are able to differentiate into valvular phenotypes of endothelial cells (CD31-green immunofluorescent stain depicted by green arrows) and interstitial cells (alpha SMA-orange immunofluorescent stain depicted by orange arrows), respectively. The white arrows in FIGS. 14C, 14D, 15C, and 15D are demonstrating the stem cells via DAPI staining.

Figures 16A, 16B, 16C, 16D, 16E:
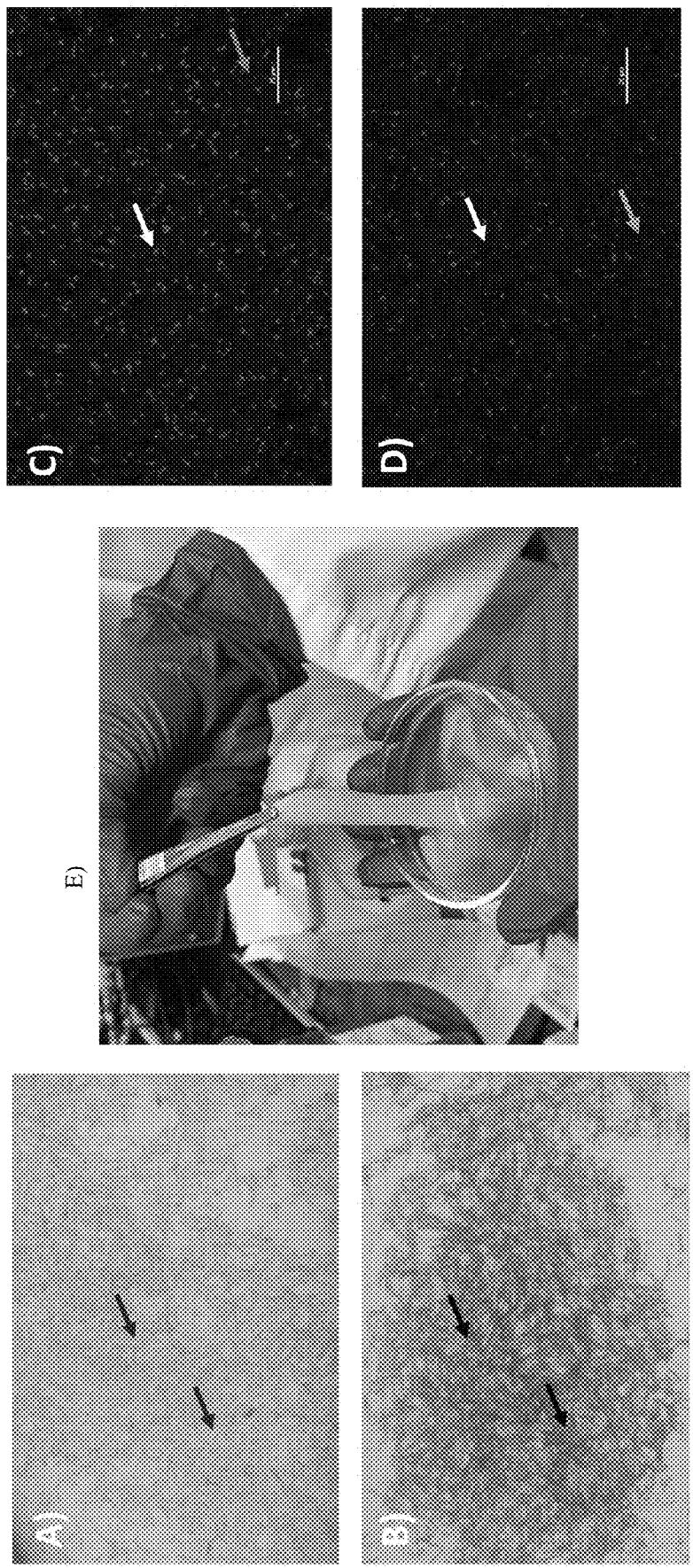
FIGS. 16A-16E show outcomes of a version 2 torpedo bioreactor.

FIGS. 16A-16E show outcomes of a version 2 torpedo bioreactor. FIG. 16 is similar to FIGS. 14 and 15. In the torpedo bioreactor this embodiment was shown to produce excess amounts of tissue (FIG. 16E), which appears to be mostly elastin (FIG. 16B). This is demonstrated by the presence of cells (FIG. 16A, 16C, 16D) as well as some phenotypic valvular cells, including endothelial and interstitial cells in FIGS. 16C and 16 D, respectively. FIGS. 2B, 2C and FIGS. 5 and 6 all underwent the decellularization protocol outlined in FIG. 4. The process of counting the cells in FIGS. 5 and 6 were the same.

In FIGS. 9-12, the bioscaffolds were stained with Movat's histological stain and processed via spatial intensity maps to determine the percentages of collagen and elastin. FIGS. 7 and 8, however, are regular (unseeded) PSIS bioscaffolds that underwent a decellularization process, while FIGS. 9-12 were seeded with stem cells and only FIGS. 11-12 underwent a decellularization protocol.

FIG. 13 shows a waveform that provided an OSI and TAWSS of 0.20 and 3.1 dynes/cm2, respectively. The PSIS bioscaffolds shown in FIGS. 14 and 15 were exposed to this waveform in FIG. 13. FIG. 16 was a by-product found in the torpedo bioreactor. FIGS. 14 -16 were assessed similarly looking at H&E and Movat's staining (FIGS. A-B) for morphology and ECM content, respectively. Moreover, the valvular phenotype was demonstrated via CD31 and alpha SMA immunofluorescence (FIGS. C-D).

The transitional term "comprising," "comprises," or "comprise" is inclusive or open -ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

EXAMPLE 1

Careful Re-Decellularization for 12 Hours with the Enhanced Retention of Bioscaffold Matrix Components Experiments were conducted to investigate the use of porcine small intestinal submucosa (PSIS; FIG. 3A) (Cor-Matrix, Roswell, Ga.) as a viable bioscaffold in an animal model. An explant of the PSIS mitral valve (11 months post-implantation) showed a chronic immune response (FIG. 3B), which was hypothesized as being due to remaining porcine cells.

Without being bound by theory, it was hypothesized that applying a cautious, yet thorough decellularization technique would further remove porcine cells while maintaining the integrity of the extracellular matrix (ECM). This experiment was designed to confirm an acellular PSIS scaffold having a structurally intact ECM suitable for implantation with reduced immune response to support proper de novo valvular tissue formation via chemotaxis.

Three strips (0.9×0.5 cm) of PSIS scaffolds were obtained from CorMatrix valves: two decellularized strips and one acellular. One of the decellularized strips was selected for further decellularization with a softer decellularization procedure (see FIG. 4). Each PSIS strip was stained with DAPI (4',6-diamidino-2-phenylindole) to detect the cell nuclei. DAPI is a fluorescent stain that binds strongly to adeninethymine-rich regions in DNA. Since DAPI can pass through an intact cell membrane, it can be used to stain both live and fixed cells. The number of cells was determined by counting the circular cells on ImageJ from the DAPI images. Specifically, FIGS. 5 and 6 DAPI images were used to get the total amount of cells shown in FIGS. 5 and 6 B, D and F. Image processing included steps of Grayscale, Adjust Threshold, and Analyze Particles. The acellular (positive control) PSIS strip had few cells compared to both the decellularized PSIS strip (negative control) and the careful re-decellularized group (see FIGS. 5A-5F and Table 1).

TABLE 1

| Cellular Count on PSIS Bioscaffold Strips | |
| --- | --- |
| Acellular n = 1 | 549 |
| Decellularized n = 1 | 12,928 |
| Careful Re-decellularized n = 1 | 4,985 |

Comparing the Decellularized bioscaffold to the Careful Re-decellularized bioscaffold, there was a 61% decrease in cellular count.

The resulting cell count of the three bioscaffolds showed that the acellular bioscaffold had the least amount of cells present while the decellularized (control) had the most. In regards to cell removal, the careful decellularization protocol resulted in a reduction in cell count in the re-decellularized bioscaffold compared to the control, decellularized bioscaffold.

The tested embodiments provide a decellularization protocol that is effective and successful in removing cells from a bioscaffold and retaining ECM integrity, which is beneficial for treating scaffolds meant for implantation and provides benefits such as de novo growth and tissue formation with either a minimal or no immune response from the host.

EXAMPLE 2

Careful Re-Decellularization for 12 Hours and 24 Hours with the Enhanced Retention of Bioscaffold Matrix Components PSIS has been investigated as a viable bioscaffold in an animal model. An explant of a PSIS mitral valve showed a chronic immune response hypothesized to be due to remaining porcine cells. A cautious yet thorough decellularization technique was employed to further remove porcine cells while maintaining the integrity of the extracellular matrix (ECM). An acellular PSIS scaffold having a structurally intact ECM was created to alleviate or remove corresponding immune response and allow for proper de novo valvular tissue formation via chemotaxis.

Strips (0.9×0.5 cm) of PSIS scaffolds were obtained from CorMatrix valves: two decellularized strips and one acellular. One of the decellularized strips was selected to undergo further decellularization with a softer decellularization procedure (see FIG. 4). Each PSIS strip was stained with Movat's to identify ECM components. Each PSIS strip was stained with DAPI to detect the cell nuclei. The amount of cells was determined based on ImageJ processing through Grayscale, Adjust Threshold, and Analyze Particles.

The acellular (positive control) PSIS strip had few cells compared to both the decellularized PSIS strip (negative control) and the careful re-decellularized group (see FIGS. 6A-6H and Table 2). Between the decellularized bioscaffold and the careful 12 hour re-decellularized bioscaffold there was a 25% decrease in the amount of cells observed and a 31% decrease compared to the careful 24 hour re-decellularized bioscaffold.

TABLE 2

| DAPI Immunofluorescence Cell Count on PSIS Cellular Count on PSIS Bioscaffold Strips | |
| --- | --- |
| Acellular (n = 3) | 1134 ± 144 |
| Decellularized (n = 3) | 2697 ± 292 |
| Careful Re-decellularized, 12 hr (n = 3) | 2093 ± 59 |
| Careful Re-decellularized, 24 hr (n = 3) | 1954 ± 474 |

The resulting cell count of the three bioscaffolds showed that the acellular bioscaffold had the least amount of cells present while the decellularized (control) had the most. In regards to cell removal, the careful decellularization protocol appears to be effective as there was a reduction in cell count in the re-decellularized bioscaffold compared to the control, decellularized bioscaffold. The 24 hour decellularization protocol has a lower cell count than the 12 hour protocol. ECM integrity analysis showed some level of disruption of matrix structure in both the 12 hour and 24 hour decellularization procedure.

Spatial intensity maps were obtained by doing image processing via a combination of ImageJ and an in-house MATLAB script. The bioscaffolds were first stained with a histological stain called Movat's, where different ECM structures can be distinguished. Elastin is stained in a black-purple color, while collagen is stained in a yellow-green color. The images were normalized, based off the control bioscaffold, and the color intensities of the components were used to quantify the percentage of ECM components present at each section of the bioscaffold. The DC control (Ver. 1) in FIGS. 7 and 8 correspond to FIG. 2A. Image 1 of the 12 hr. decellularization in FIGS. 7 and 8 corresponds to FIG. 2B. Image 1 of the 24 hr. decellularization in FIGS. 7 and 8 correspond to FIG. 2C. Based on these results it was determined that the 24 hr decellularization protocol was able to remove more cells, while maintaining the ECM structure and components.

Example 6 shows results comparing ECM content after careful decellularization protocol with a healthy juvenile, non-human primate's (juvenile baboon, approximately 14 months old), native mitral valve's ECM composition.

The tested embodiments provide a decellularization protocol that is effective and successful in removing cells from a bioscaffold and retaining ECM integrity beneficial for treating scaffolds meant for implantation to provide benefits such as de novo growth and tissue formation with either a minimal or no immune response from the host.

EXAMPLE 3

Tensile Testing of Samples in Radial and Circumferential Directions

Embodiments of the subject invention provide elastin-rich tissues of the same species as the host in which it will be implanted for cardiovascular repair/regenerative applications, using stem cells and safely removing the stem cells from the engineered tissue matrix prior to implantation. The results presented in this example focus on the careful removal of the stem cells (e.g., decellularization) while leaving the engineered tissues or engineered extracellular matrix (ECM) functionally intact. Tested samples provide increased production of elastin within a tissue engineered construct, which can help accelerate the regeneration of cardiovascular or other tissues after the construct is implanted for repair/regeneration purposes.

The bioscaffolds remain intact after careful decellularization protocol, meaning that the structure and function of the bioscaffold does not change significantly ($p > 0.05$). Quantitatively, embodiments have demonstrated that bioscaffolds remained intact through mechanical testing. As detailed in Example 5, it was found that there was no significant difference ($p > 0.05$) between the stiffness or max tensile stress between control and treated (careful decellularized) groups, meaning they are "intact."

TABLE 3

| Treatment | Direction | Linear Stiffness | Avg. Linear Stiffness +/− SEM | Max Tensile Stress | Avg. Max Tensile Stress +/− SEM |
|---|---|---|---|---|---|
| Control | Radial | 14.84 | 15.01 +/− 2.22 | 2.13 | 2.71 +/− 0.32 |
|  |  | 18.94 |  | 2.80 |  |
|  |  | 11.26 |  | 3.22 |  |
|  | Circumferential | 20.51 | 21.79 +/− 0.71 | 1.67 | 1.67 +/− 0.005 |
|  |  | 22.96 |  | 1.67 |  |
|  |  | 21.89 |  | 1.68 |  |
| TX100 | Radial | 8.71 | 7.32 +/− 2.94 | 2.06 | 2.21 +/− 0.16 |
|  |  | 1.67 |  | 2.04 |  |
|  |  | 11.58 |  | 2.52 |  |
|  | Circumferential | 35.78 | 35.64 +/− 2.81 | 2.13 | 2.22 +/− 0.11 |
|  |  | 40.44 |  | 2.43 |  |
|  |  | 30.72 |  | 1.097 |  |

FIGS. 1A-1B and Table 3 show that the decellularization process retains the integrity of fibers in the tissue-engineered construct and re-aligns fibers from the radial to circumferential direction resulting in a more isotropic material with respect to maximum strength. While not being bound by theory, these fibers appear to not be lost but rather, they are re-distributed. The protocol safely removes the stem cells while retaining the critical increased tissue-engineered elastin content that the cells had produced in bioreactor dynamic tissue culture conditions.

After decellularization tissue fibers in the TX100 group were observed to be re-aligned from the radial direction to the circumferential direction, making the constructs more isotropic in terms of their strength (Max Tensile Stress). The greater density of fibers shown in the figure on the bottom left was a result of this fiber re-alignment, which also suggests that the vertical dimension in the figure is the circumferential direction.

EXAMPLE 4

Measurement of Enhanced Retention of Elastin and Collagen Bioscaffold Matrix Components Following Careful Re-Decellularization Protocol Data was collected to show collagen and elastin percentage in untreated engineered tissues in the Control Group as compared to collagen and elastin percentage in decellularized engineered tissues in the TX100 Group.

FIG. 7 and FIG. 8 demonstrate the effect of a decellularization protocol according to an embodiment of the subject invention on raw bio-scaffolds without any cells. The bioscaffold is a PSIS. The images indicate that the treated (decellularized) samples did have substantial alterations in both collagen (overall increase) and elastin (overall decrease) content compared to an untreated (control) sample. This suggests that the decellularization protocol does alter the composition of collagen and elastin in bioscaffold ECM.

FIG. 9 and FIG. 10 (untreated engineered tissues), and FIG. 11 and FIG. 12 (previously-decellularized engineered tissues) show the results summarized in Table 4 for a decellularization protocol according to an embodiment of the subject invention when applied on engineered tissues produced via seeding of stem cells on PSIS and culturing these constructs for 8 days. Compared to untreated tissues, the treated tissues exhibit virtually no cells, showing that the decellularization did remove the stem cells. Both collagen and elastin content were found to be not significantly different ($p > 0.05$) after decellularization treatment. This decellularization protocol is safe at removing stem cells while retaining both the engineered elastin and engineered collagen in the ECM.

Given that native elastin and collagen ECM components in raw PSIS were significantly altered after decellularization treatment, but there were insignificant alterations ($p > 0.05$) in both engineered elastin and engineered collagen in the stem-cell secreted tissues, engineered tissues respond favorably (e.g., no alterations in both collagen and elastin) to the decellularization protocol whereas raw bio-scaffolds based on native tissue architecture do not respond favorably (e.g., substantial alterations in both collagen and elastin). Thus, the method results in an advantageous result when applied to engineered tissue constructs as compared to similar native or naturally occurring tissues.

TABLE 4

|  | Elastin (%) | | Collagen (%) | |
| --- | --- | --- | --- | --- |
|  | Control | TX100 | Control | TX100 |
|  | 16.7 | 18.85 | 23.64 | 36.95 |
|  | 19.16 | 22.46 | 33.35 | 22.42 |
|  | 22.44 | 29.14 | 30.71 | 27.65 |
|  | 5.61 | 21.68 | 23.64 | 33.73 |
|  | 30.49 | 18.16 | 27.54 | 35.7 |
|  | 23.22 |  | 19.5 |  |
| Average | 19.603 | 22.058 | 26.397 | 31.29 |
| Alpha value |  | 0.05 |  |  |
| P-value (two tailed) |  | 0.568 |  | 0.182 |

EXAMPLE 5

Mechanical Testing Results Following Careful Re-Decellularization Protocol

Engineered tissues derived from stem cells which were deposited on porcine small intestinal submucosa (PSIS) bio-scaffolds were mechanically tested with (Triton-X-100) and without (control) a careful decellularization protocol.

Uniaxial tensile tests were performed on PSIS strips seeded with hBMSCs and strips that underwent decellularization using 1% Triton X-100.

There is no statistically significant difference between the treatments regarding linear stiffness and max stress in either direction.

The findings showed that the mechanical properties in terms of the linear stiffness and the maximum tensile stress were unaffected by the careful decellularization process.

TABLE 5

| Treatment | Direction | Average Linear Stiffness +/- SEM (MPa) | Average Max Tensile Stress +/- SEM (MPa) |
| --- | --- | --- | --- |
| Control | Circumferential | 16.142 +/- 1.792 | 2.715 +/- 0.316 |
|  | Axial | 9.645 +/- 0.818 | 1.674 +/- 0.004 |
| Triton X-100 | Circumferential | 21.093 +/- 3.050 | 2.984 +/- 0.129 |
|  | Axial | 9.589 +/- 1.248 | 2.396 +/- 0.194 |
| Comparison Group | | | t-Test p-value |
| Axial Linear Stiffness | | | 0.973 (>0.05) |
| Circumferential Linear Stiffness | | | 0.256 (>0.05) |
| Axial Max Stress | | | 0.066 (>0.05) |
| Circumferential Max Stress | | | 0.488 (>0.05) |

EXAMPLE 6

Comparison of Native Baboon Mitral Valve Explant and ECM-Enriched Psis Mitral Valve Explant Following Careful Re-Decellularization Protocol Elastin and Collagen content of explants was measured in carefully decellularized engineered cardiovascular/valvular tissues and compared to the native mitral heart valve of a juvenile (~14 months old) non-human primate. Elastin content was in similar composition in the engineered tissues after careful decellularization (ECM-enriched), compared to the native mitral valve (native); (p<0.05). Collagen content was similar composition in the engineered tissues after careful decellularization (ECM-enriched), compared to the native mitral valve (native); (p<0.05).

There is no statistically significant difference between the native baboon mitral valve explant and our ECM-enriched PSIS mitral valve explant that underwent careful decellularization prior to surgery regarding both elastin and collagen content.

TABLE 6

|  |  | ELASTIN (%) | | COLLAGEN (%) | |
| --- | --- | --- | --- | --- | --- |
|  |  | Native | ECM-Enriched | Native | ECM-Enriched |
| Section | 1 | 42.81 | 48.81 | 33.88 | 23.41 |
|  | 2 | 21.43 | 48.09 | 21.66 | 21.03 |
|  | 3 | 38.36 | 28.36 | 29.48 | 17.48 |
|  | 4 | 47.77 | 50.92 | 35.29 | 27.74 |
|  | 5 | 39.97 | 42.9 | 31.07 | 36.9 |
|  | 6 | — | 44.29 | — | 39.16 |
|  | 7 | — | 28.36 | — | 17.88 |
| Average |  | 38.068 | 41.67571429 | 30.276 | 26.22857143 |
| P-value (two-tailed) |  | 0.546 (>0.05) | | 0.346 (>0.05) | |

It should be understood that the examples and embodiments described herein are for illustrative purposes only and that various modifications or changes in light thereof will be suggested to persons skilled in the art and are to be included within the spirit and purview of this application and the scope of the appended claims.

All patents, patent applications, provisional applications, and publications referred to or cited herein are incorporated by reference in their entirety, including all figures and tables, to the extent they are not inconsistent with the explicit teachings of this specification.

What is claimed is:

1. An enriched decellularized bioscaffold implant for implantation in a patient, the bioscaffold implant comprising:
   a decellularized tissue matrix; and
   an engineered extracellular matrix (ECM) component generated by stem cells and comprising elastin and collagen,
   the bioscaffold implant being decellularized,
   the decellularized bioscaffold implant having a percentage elastin after decellularization not less than its percentage elastin before decellularization,
   the decellularized bioscaffold implant having a percentage collagen after decellularization not less than its percentage collagen before decellularization,
   the bioscaffold implant having a cell count includign the stem cells after decellularization at least 50% less than its cell count including the stem cells after generation of the elastin and collegen but before decellularization,
   the decellularized tissue matrix being syngeneic or xenogeneic to the patient, and
   the stem cells being allogeneic, autologous, or syngeneic to the patient.

2. The bioscaffold implant according to claim 1, the decellularized tissue matrix being porcine small intestinal submucosa (PSIS).

3. The bioscaffold implant according to claim 2, the patient being a human and the engineered ECM component comprising at least 8% allogeneic elastin.

4. The bioscaffold implant according to claim 1, the decellularized tissue matrix having a cylindrical shape comprising a radial direction and a circumferential direction.

5. The bioscaffold implant according to claim 4, the decellularized tissue matrix having a measurable average maximum tensile stress in the circumferential direction, which is at least 80% of a measurable average maximum tensile stress of the decellularized tissue matrix in the radial direction.

6. A first group comprising a multiplicity of enriched decellularized bioscaffold implants, each enriched decellularized bioscaffold implant being an enriched decellularized bioscaffold implant according to claim 1, the first group having an average percentage elastin not less than an average percentage elastin of a control group comprising a multiplicity of enriched but non-decellularized bioscaffold implants,
- each enriched but non-decellularized bioscaffold implant in the control group comprising an engineered ECM component comprising elastin and collagen and being generated by control group stem cells through the same process used to generate the engineered ECM in each enriched decellularized bioscaffold implant in the first group, and
- a first average cell count of the first group including the stem cells after decellularization being at least 50% less than a second average cell count of the control group including the control group stem cells after generation of the elastin and collagen but prior to or absent any decellularization of each enriched but non-decelluarized bioscaffold implant in the control group.

7. The first group according to claim 6, having an average percentage collagen not less than an average percentage collagen of the control group.

8. A method of fabricating an enriched decellularized bioscaffold implant for implantation in a patient, the method comprising:
- providing a tissue matrix;
- exposing the tissue matrix to stem cells in a bioreactor under conditions sufficient to generate an engineered extracellular matrix (ECM) component in the tissue matrix and comprising elastin and collagen; and
- decellularizing the tissue matrix to remove the stem cells while maintaining the engineered ECM component in the tissue matrix,
- the conditions sufficient to generate an engineered ECM component in the tissue matrix comprising mechanical stimulation at a targeted fluid-induced oscillatory shear stress range having an oscillatory shear index (OSI) in a range of from 0.18 to 0.23.

9. The method according to claim 8, the tissue matrix being xenogeneic to the patient.

10. The method according to claim 9, the stem cells being allogeneic to the patient.

11. The method according to claim 10, the tissue matrix comprising porcine small intestinal submucosa (PSIS).

12. The method according to claim 11, the engineered ECM component being allogeneic to the patient and comprising elastin, collagen, and glycosaminoglycans.

13. The method according to claim 12, the engineered ECM component being elastin.

14. The method according to claim 12, the engineered ECM component being collagen.

15. The method according to claim 8, the OSI being in a range of from 0.19 to 0.21.

16. A decellularized bioscaffold implant for implantation in a patient, the bioscaffold implant comprising:
- a decellularized tissue matrix; and
- an engineered extracellular matrix (ECM) component generated by stem cells,
- the engineered ECM component comprising elastin and collagen,
- the patient being a human patient,
- the stem cells being allogeneic to the patient,
- the decellularized tissue matrix being porcine small intestinal submucosa (PSIS),
- the decellularized tissue matrix having a cylindrical shape comprising a radial direction and a circumferential direction,
- the decellularized tissue matrix having a measurable average maximum tensile stress in the circumferential direction, which is at least 80% of a measurable average maximum tensile stress of the decellularized tissue matrix in the radial direction,
- the decellularized bioscaffold implant having a percentage elastin after decellularization not less than its percentage elastin before decellularization,
- the decellularized bioscaffold implant having a percentage collagen after decellularization not less than its percentage collagen before decellularization, and
- the decellularized bioscaffold implant having a cell count after decellularization at least 50% less than its cell count after generation of the elastin and collagen but before decellularization.

* * * * *